(12) United States Patent
Stowell

(10) Patent No.: US 12,004,958 B2
(45) Date of Patent: Jun. 11, 2024

(54) ORTHOPEDIC IMPLANTS AND TOOLS

(71) Applicant: Lee Stowell, Coeur d'Alene, ID (US)

(72) Inventor: Lee Stowell, Coeur d'Alene, ID (US)

( * ) Notice: Subject to any disclaimer, the term of this patent is extended or adjusted under 35 U.S.C. 154(b) by 0 days.

(21) Appl. No.: 17/836,839

(22) Filed: Jun. 9, 2022

(65) Prior Publication Data
US 2022/0395375 A1 Dec. 15, 2022

Related U.S. Application Data

(60) Provisional application No. 63/208,960, filed on Jun. 9, 2021.

(51) Int. Cl.
*A61F 2/38* (2006.01)
*A61F 2/30* (2006.01)

(52) U.S. Cl.
CPC .. *A61F 2/3804* (2013.01); *A61F 2002/30403* (2013.01); *A61F 2002/30433* (2013.01); *A61F 2002/30593* (2013.01); *A61F 2002/30774* (2013.01); *A61F 2002/3827* (2013.01)

(58) Field of Classification Search
CPC .. A61F 2/38; A61F 2/3804; A61F 2002/3809; A61F 2002/3813; A61F 2002/3818; A61F 2002/3822; A61F 2002/3827; A61F 2002/3831
See application file for complete search history.

(56) References Cited

U.S. PATENT DOCUMENTS

| | | | | |
|---|---|---|---|---|
| 9,579,208 | B2 * | 2/2017 | Katrana | A61F 2/4637 |
| 9,636,228 | B2 * | 5/2017 | Leibel | A61F 2/3804 |
| 2005/0216090 | A1 | 9/2005 | Odriscoll et al. | |
| 2012/0083892 | A1 | 4/2012 | Kehres et al. | |
| 2012/0209392 | A1 * | 8/2012 | Angibaud | A61F 2/4081 |
| | | | | 623/19.11 |
| 2019/0269516 | A1 | 9/2019 | Hodorek et al. | |

OTHER PUBLICATIONS

International Search Report dated Nov. 30, 2022 received in PCT/US2022/032875.

* cited by examiner

*Primary Examiner* — Bruce E Snow
(74) *Attorney, Agent, or Firm* — Dorsey & Whitney LLP

(57) ABSTRACT

A prosthetic device can include a neck defining an upper surface and a sidewall extending from the upper surface, an opening defined by the sidewall and extending into the neck, one or more interior surfaces extending into the neck from the opening to define a female receiving cavity, and a radial head including a male protrusion received within the female receiving cavity through the opening.

17 Claims, 35 Drawing Sheets

ORTHOPEDIC IMPLANTS AND TOOLS

CROSS-REFERENCE TO RELATED APPLICATIONS

This application claims priority to U.S. Provisional Patent Application No. 63/208,960 filed on Jun. 9, 2021, the disclosure of which is incorporated herein, in its entirety, by this reference.

FIELD

The present disclosure relates generally to orthopedic implants and tools. More particularly, the present disclosure relates to radial head prostheses and surgical tools for radial head arthroplasty and revision procedures.

BACKGROUND

Radial head arthroplasty procedures are complex and present a high risk of damaging bone, cartilage, and other soft tissue surrounding the proximal head of the radius. Current prosthesis and surgical tools can lead to a number of short term and long term complications. For example, currently available radial head prostheses can become loose over time, which is painful for the patient and may require radial head resection surgery later on. Current prostheses can also lead to elbow join stiffness, humeroradial conflict, and general instability. This can be due to a number of factors, including prosthetic implants that do not promote sufficient short-term or long-term mechanical or biological fixation to the radius. Thus, currently available prostheses can loosen over time to the point that revision surgery is necessary, which raises more risks and causes more pain to the patient.

Both radial head arthroplasty and revision/resection surgeries are technically difficult procedures that require many different tools. Using currently available tools and prostheses, it is difficult to correctly position the radial head implant to interface naturally with the humerus. Also, fixing radial head implants within the radius, including mechanical immediate press-fit fixation and long-term mechanical and biological fixation, is difficult to achieve with the current implants and surgical tools. In addition, both the insertion and resection of radial head prosthetics during arthroplasty and revision procedures, respectively, puts the radius and surrounding tissue, such as nerves, cartilage, and tendons, surrounding the radius, at risk for damage, including bone fracture.

Thus, there is a current need for orthopedic implants, including radial head prostheses for radial head arthroplasty procedures, that are easy to use, provide reproducible results and outcomes, ensure long term biological fixation and immediate press-fit fixation, and which also preserve the patient's natural bone structure as much as possible. In addition, there is a need in the art for new and improved tools for performing radial head arthroplasty and revision procedures that reduce the risk of damage to the radius and other bones, nerves, and cartilage surrounding the radius.

SUMMARY

The present disclosure relates generally to orthopedic implants and tools. More particularly, the present disclosure relates to radial head prostheses and surgical tools for radial head arthroplasty and revision procedures. In at least one embodiment of the present disclosure, a prosthesis includes: a neck defining a sidewall extending circumferentially around the neck, the sidewall defining a sidewall opening; a female receiving cavity defined by one or more interior surfaces extending into the neck from the sidewall opening; and a stem extending from the neck.

In at least one embodiment of the present disclosure, a prosthesis includes: a neck defining an upper surface and a sidewall extending downward from the upper surface; an opening defined by the sidewall and extending into the neck, the opening having an upper portion and a lower portion, wherein the lower portion extends laterally beyond a width of the upper portion.

In at least one embodiment of the present disclosure, a prosthetic device includes: a neck defining an upper surface and a sidewall extending from the upper surface; an opening defined by the sidewall and extending into the neck; one or more interior surfaces extending into the neck from the opening to define a female receiving cavity; and a radial head including a male protrusion received within the female receiving cavity through the opening.

BRIEF DESCRIPTION OF THE DRAWINGS

The disclosure will be readily understood by the following detailed description in conjunction with the accompanying drawings, wherein like reference numerals designate like structural elements, and in which.

DETAILED DESCRIPTION

Figure 1:
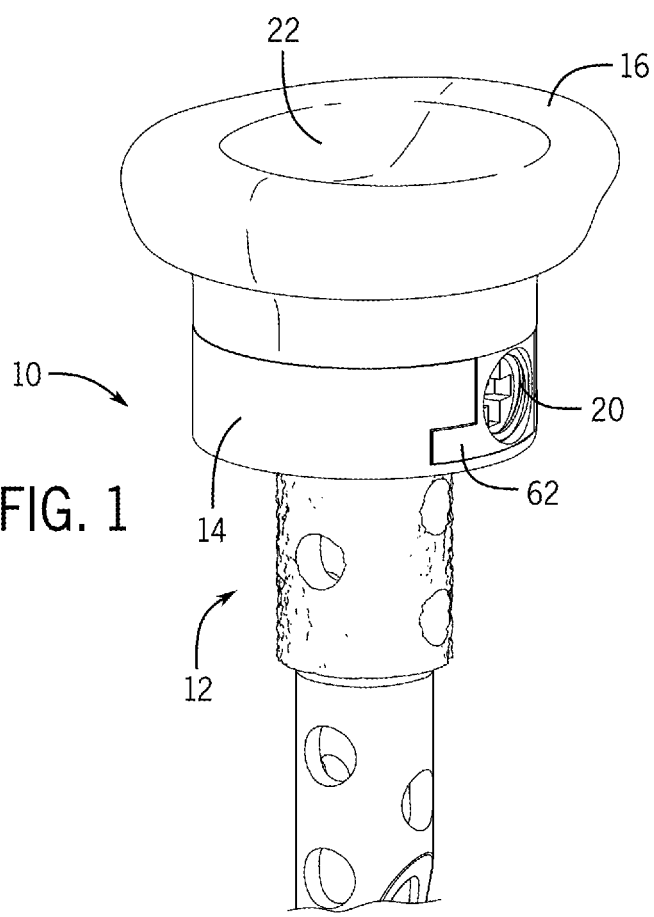
FIG. 1 illustrates a perspective view of an embodiment of a prosthesis having a radial head component.

Reference will now be made in detail to representative examples illustrated in the accompanying drawings. It should be understood that the following descriptions are not intended to limit the embodiments to one preferred embodiment. To the contrary, it is intended to cover alternatives, modifications, and equivalents as can be included within the spirit and scope of the described embodiments, as defined by the appended claims.

Embodiment of implants and tools described herein provide solutions to the problems in the art noted above. For example, in at least one embodiment, a prosthetic implant includes a neck and a stem extending from the neck. In at least one embodiment, the neck has a sidewall extending circumferentially around the neck, an opening defined by the sidewall, and one or more interior surfaces defining a female receiving cavity. A radial head component having a male protrusion can be coupled to the neck of the prosthetic implant with the male protrusion received and locked into the female receiving cavity of the neck. The opening in the sidewall of the neck of the prosthetic implant allows the radial head to be side-loaded into the neck and coupled to the stem.

This side-load configuration of the prosthetic implants described herein reduces the space needed above the stem or neck of the prosthetic implant for a surgeon to implant the prosthetic radial head. Reducing the space needed for implantation reduces the risk of damaging the radius and surrounding bones tissue, such as cartilage, tendons, and other soft tissue surrounding the radius. The surgeon does not need to utilize much space above the stem to secure the prosthetic radial head onto the stem after the stem is inserted into the reamed canal of the radius because the radial head can be loaded into and coupled with the stem through a sidewall of the stem or neck of the stem.

In addition, embodiments of prostheses described in the present disclosure include stems having distal hooked or curved geometries that reduce the space proximal to the radius needed by a surgeon to insert the stem into the canal of the radius. That is, using the curved or hooked geometries of the prostheses described herein, the surgeon can initially position the stem at an angle relative to the radius and hook the stem into the canal. Accordingly, prostheses of the present disclosure can include longer stems for prostheses that maintain a ratio or quotient of the height of the head to the length of the stem of the prosthesis to less than or equal to about 0.4. Longer stems are advantageous for more effective short term and long term mechanical and biological fixation with the radius.

Some embodiments of prostheses described herein also include stems that promote bone-to-bone continuity such that bone grows from one side of the stem, through one or more apertures into a hollow internal volume of the stent, and back out the stent through one or more other apertures. A proximal portion of the stems described herein can promote press-fit fixation within a bone where a hoop-stress of the bone pressing inward on the stem fixes the stem in place.

In some embodiments, the stems can include apertures that extend through the stem and into the inner volume of hollow stems, to provide access for bone on-growth into the stem. This also improves long-term biological fixation.

Therefore, using embodiments of prostheses described herein, surgeons minimize the rate of painful loosening over time of the prostheses, minimize instability and joint stiffness, and minimize the risk of bone fracture during radial head arthroplasty and revision procedures.

In cases where revision or resection of the radial head prosthesis is required, the embodiments of prostheses described herein simplify the revision procedure and minimize the risk of damage that can occur to the radius and surrounding bones and tissues. For example, at least one embodiment of the present disclosure includes a resection cap that can be inserted into the female receiving cavity of the stem or neck of the stem of the prosthesis. This resection cap can be side-loaded similar to the side-loading configuration of the radial head coupled to the stem as described above.

During a revision or resection procedure, the surgeon simply laterally pulls the radial head from the stem by unscrewing a locking screw to uncouple the radial head from the neck of the stem. Again, this can be done with minimal to no interference with the space above (proximal) to the radial head prosthesis. Next, the surgeon can side-load the resection cap into the cavity of the neck of the stem through an opening in the sidewall thereof and couple the cap to the stem using the same or similar screw. Again, the insertion of the resection cap can be done without interfering with any space above the stem. In addition, the stem need not even be removed during the resection/revision procedure. Rather, the insertion cap forms a flush, continuous surface with the neck of the stem such that removal of the stem is not necessary after removal of the radial head.

Thus, revision procedures using embodiments of the resection caps and prostheses described herein reduce the risk of fracturing the radius and damaging surrounding bones and tissues during the procedure.

radial head arthroplasty and revision procedures described herein that utilize embodiments of devices, systems, and components described in the present disclosure, are reproducible enable surgeons to achieve reliable immediate press-fit and long-term biological fixation of prostheses with the radius.

In addition to embodiment of prostheses and associated components disclosed herein, surgical tools are described that simplify radial head arthroplasty and revision procedures. For example, in at least one embodiment, a radial head sizing tool is provided that only requires a single insertion of two opposing stop plates. The stop plates are moved away from each other until they make contact with the proximal end of the radius and the distal end of the humerus. The tool includes calibrated measurement indicia that indicate to the surgeon the appropriate size of the radial head to be implanted. This can be done without the need for multiple insertions of multiple measurement blocks or gauges, which increase the risk of damaging nerves, cartilage, and other soft tissue disposed around and between the gap separating the radius and the humerus.

In addition, embodiments of the present disclosure include rifled graft packing tools that effectively prepare the stem of the prosthesis with bone graft material and all-in-one sizing blocks, stem insertion handles, and strike plates that simplify the preparation and insertion of the stem while minimizing the risk of dropping or otherwise damaging the prosthetic stem during preparation. In addition, the present disclosure describes embodiments of reamers and planers that improve bone compaction and surface preparation for forming canals and resected surfaces configured to receive radial head prostheses.

These and other embodiments are discussed below with reference to FIGS. 1-29. However, those skilled in the art will readily appreciate that the detailed description given herein with respect to these FIGS. is for explanatory purposes only, and should not be construed as limiting.

Also, while embodiments of devices, systems, and methods of the present disclosure are described in the context of radial head arthroplasty and revision procedures, the devices, systems, and methods described herein are not limited to such applications. Indeed, embodiments of devices, systems, and methods described herein can be used for other procedures, such as shoulder arthroplasty procedures, knee arthroplasty procedures, or other orthopedic procedures to provide the same advantages and improvements thereto.

Figure 2:
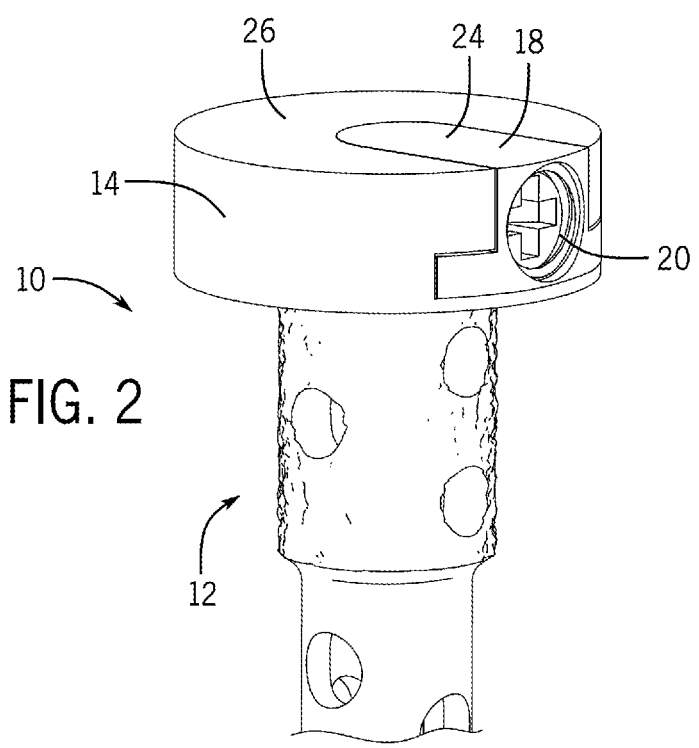
FIG. 2 illustrates a perspective view of an embodiment of a prosthesis having a resection cap component.

Turning now to the figures, FIG. 1 illustrates an exemplary embodiment of a radial head prosthesis 10 configured for use in radial head arthroplasty procedures. In at least one embodiment, prosthesis 10 includes an elongate stem 12 extending from a neck 14 that can be selectively coupled with radial head 16 is shown in FIG. 1. In at least one embodiment, a diameter of neck 14 is greater than a diameter of stem 12 such that neck 14 extends radially outward from stem 12. In such embodiments, a lower surface of neck 14 is configured to rest on a proximal resected surface of a patient's radius. Alternatively, as shown in FIG. 2, neck 14 of prosthesis 10 can be selectively coupled with a resection arthroplasty cap 18, otherwise referred to as a resection cap or simply as a cap. In either case, a screw 20 can couple either radial head 16 or resection cap 18 to neck 14 of prosthesis 10.

Radial head 16, when coupled to neck 14 of prosthesis 10, extends upward and above neck 14. In at least one embodiment, a top surface 22 of radial head 16 is formed having a typography that complements the anatomical topography of the resected head to compliment the distal end of a patient's humerus bone, specifically the capitulum of the humerus. In contrast, when resection cap 18 is coupled with neck 14 of prosthesis, as shown in FIG. 2, an upper surface 24 of resection cap 18 may be flush or substantially flush with an upper surface 26 of neck 14.

Figure 3:
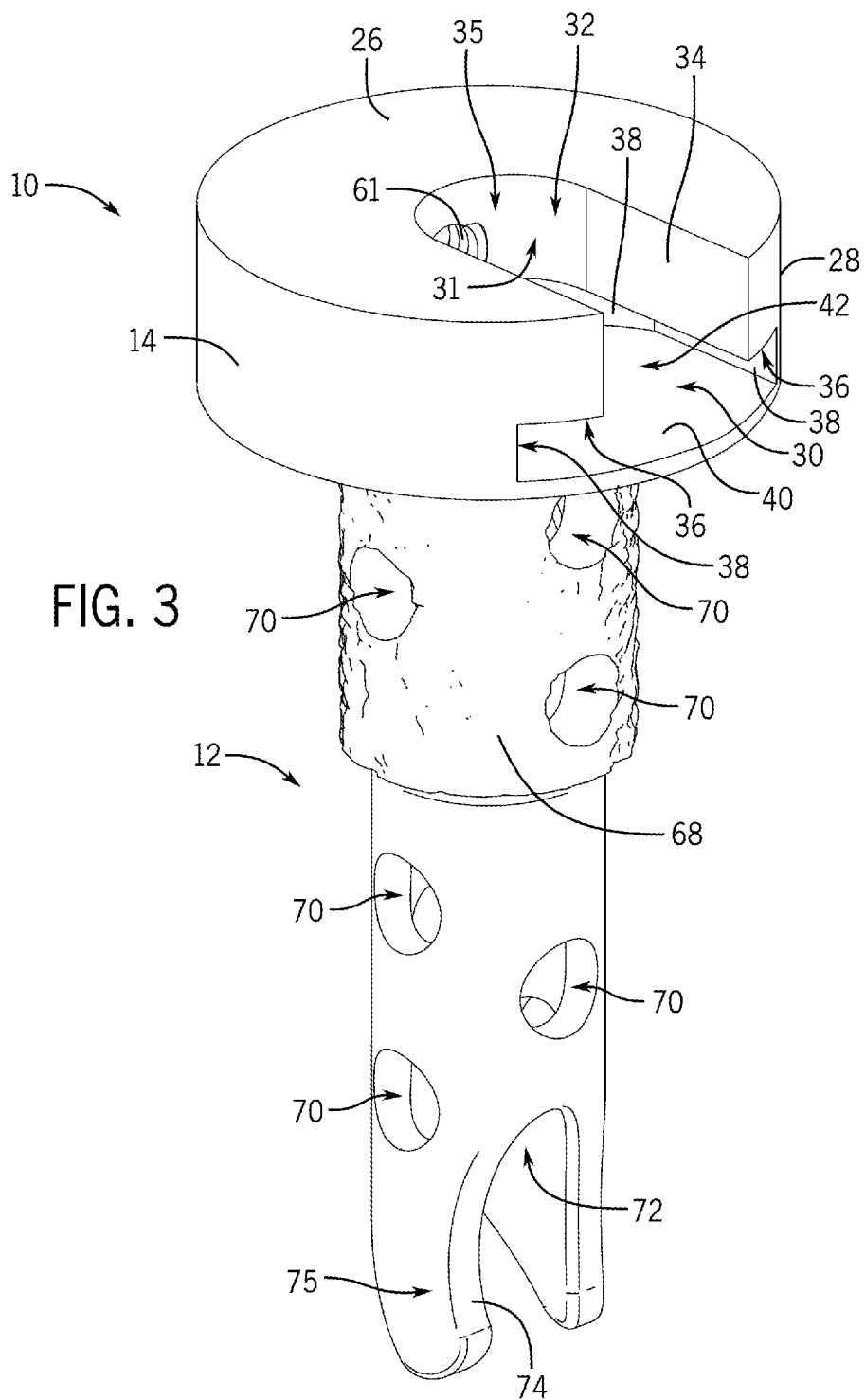
FIG. 3 illustrates a perspective view of an embodiment of a prostheses without a radial head or resection cap component.

FIG. 3 illustrates a perspective view of prosthesis 10 without radial head 16 or resection cap 18 coupled thereto. In at least one embodiment, neck 14 of prosthesis 10 includes an outer perimeter surface or sidewall 28 extending circumferentially and at least partially around neck 14. In at least one embodiment, sidewall 28 defines a sidewall opening 30 and upper surface 26 of neck 14 defines an upper surface opening 31. In addition, in at least one embodiment, one or more interior surfaces that extend from sidewall opening 30 and upper surface opening 31 to define a female receiving cavity 32.

For example, in at least one embodiment, a first interior surface 34 extends generally downward from upper surface 26 of neck 14, which defines upper surface opening 31, thus forming a first portion 35 of female receiving cavity 32. Additionally, a second interior surface 36 may extend laterally outward from first interior surface 34 and a third interior surface 38 may extend generally downward from second interior surface gg. Third interior surface 38 may extend between second interior surface 36 and fourth interior surface 40, with fourth interior surface 40 defining a lower boundary or end of female receiving cavity 32. In at least one embodiment, second, third, and fourth interior surfaces 34, 38, and 40, respectively, form a second portion 42 of female receiving cavity 32. In addition, at least one embodiment of prosthesis 10 includes a threaded opening or hole 61 extending into neck 14 from one or more interior surfaces defining female receiving cavity 32.

Figure 4A:
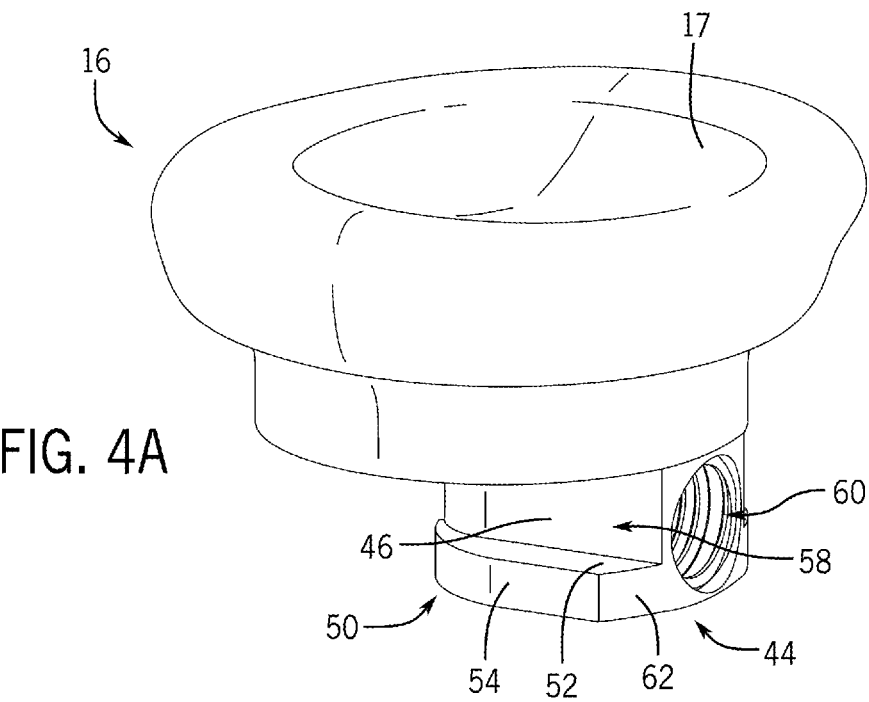
FIG. 4A illustrates a top perspective view of an embodiment of a radial head component of a prosthesis.
Figure 4B:
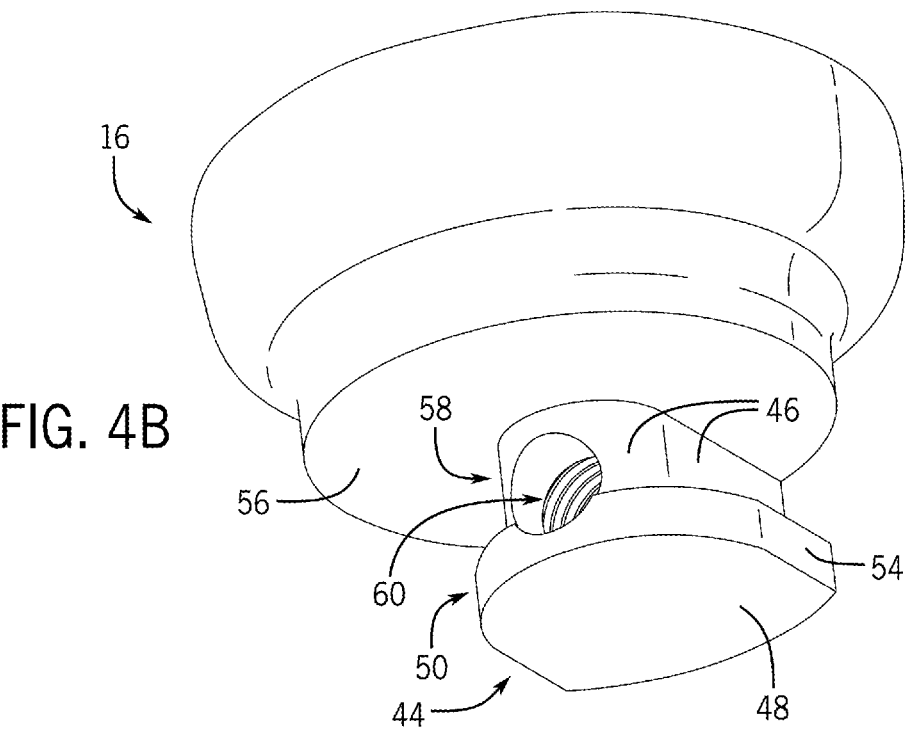
FIG. 4B illustrates a bottom perspective view of an embodiment of a radial head component of a prosthesis.

Female receiving cavity 32 may be configured to receive a male protrusion 44 of an embodiment of radial head 16 such that radial head 16 can be coupled to neck 14 of prosthesis 10 as shown in FIG. 1. For example, FIGS. 4A and 4B illustrate top and bottom perspective views, respectively, of radial head 16 with male protrusion 44 extending therefrom. In the illustrated embodiment, male protrusion 44 includes a first outer surface 46 extending generally downward from a lower surface 56 of radial head 16. Additionally, in at least one embodiment, second exterior surface 52 of male protrusion 44 extends generally outward from first exterior surface 46 and between first exterior surface 46 and third exterior surface 54, which extends generally downward from second exterior surface 52. A fourth exterior surface 48 of male protrusion 44 may extend laterally from third exterior surface 54 and define a lower boundary or end of male protrusion 44.

In at least one embodiment, second, third, and fourth exterior surfaces 52, 54, and 48, respectively, define shelf portion 50 of male protrusion 44 that expands laterally outward from a first portion 58 of male protrusion 44. In addition, at least one embodiment of radial head 16 includes a through-hole 60 extending horizontally through male protrusion 44, as shown in FIGS. 4A and 4B. In at least one embodiment, through-hole 60 is at least partially threaded.

In at least one embodiment, radial head 16 can include or define an upper surface 17 having a topography complimentary to the topography of a distal end of a humerus of a patient. The topography of upper surface 17 can vary but may include an anatomical three-dimensional shape and curvature to compliment the three-dimensional shape and curvature of a distal end of a humerus. In this way, when inserted to fit against the end of the humerus, a more natural interface and relative positioning between radial head 16 and the humerus can be accomplished.

Figure 4C:
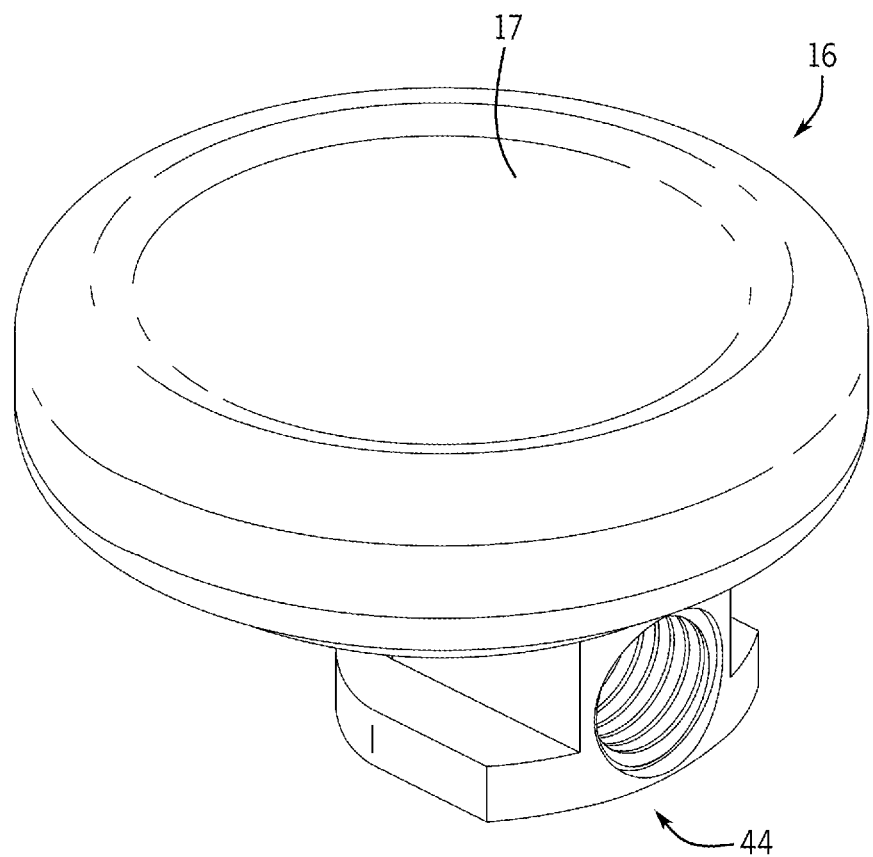
FIG. 4C illustrates a top perspective view of an embodiment of a radial head component of a prosthesis.

FIG. 4C illustrates another embodiment of a radial head 16 with male protrusion 44 extending therefrom. In the illustrated embodiment, male protrusion 44 can include similar or the same features and configuration as male protrusion 44 shown in FIGS. 4A and 4B. Upper surface 17 of radial head 17 shown in FIG. 4C can include a circular, concave topography that is symmetrical about any plane or axis normal to upper surface 17. This can be referred to as a non-anatomical radial head 17, which is not necessarily formed to compliment the natural anatomical topography of the distal end of a humerus. Such non-anatomical radial heads 16 shown in FIG. 4C can be used interchangeably with any other component of prostheses and devices described herein, in place of anatomical radial heads 16 as shown in FIGS. 4A and 4B.

Figure 5A:
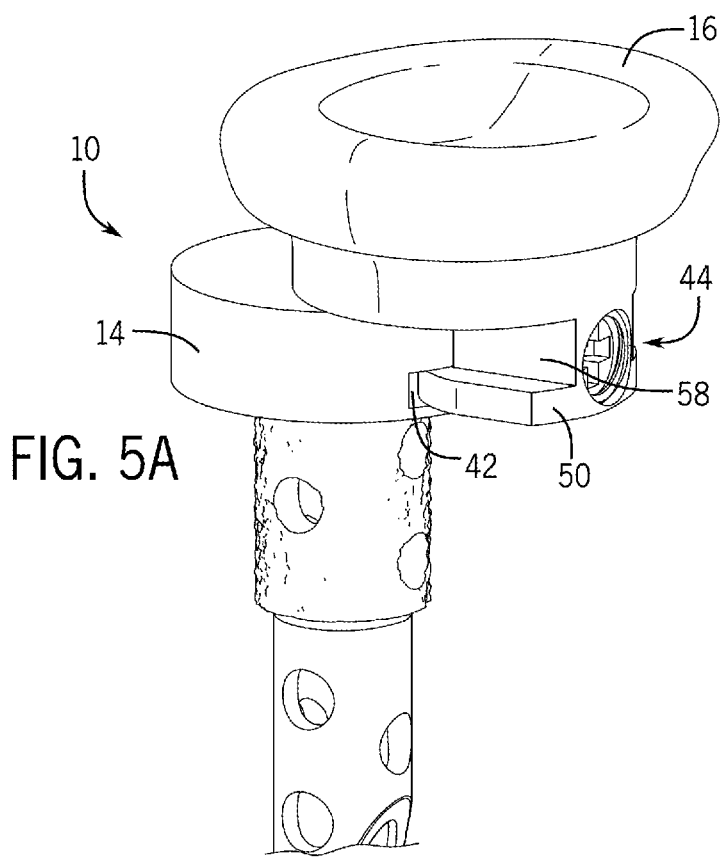
FIG. 5A illustrates an embodiment of a radial head component being coupled to the neck of a prosthesis.
Figure 5B:
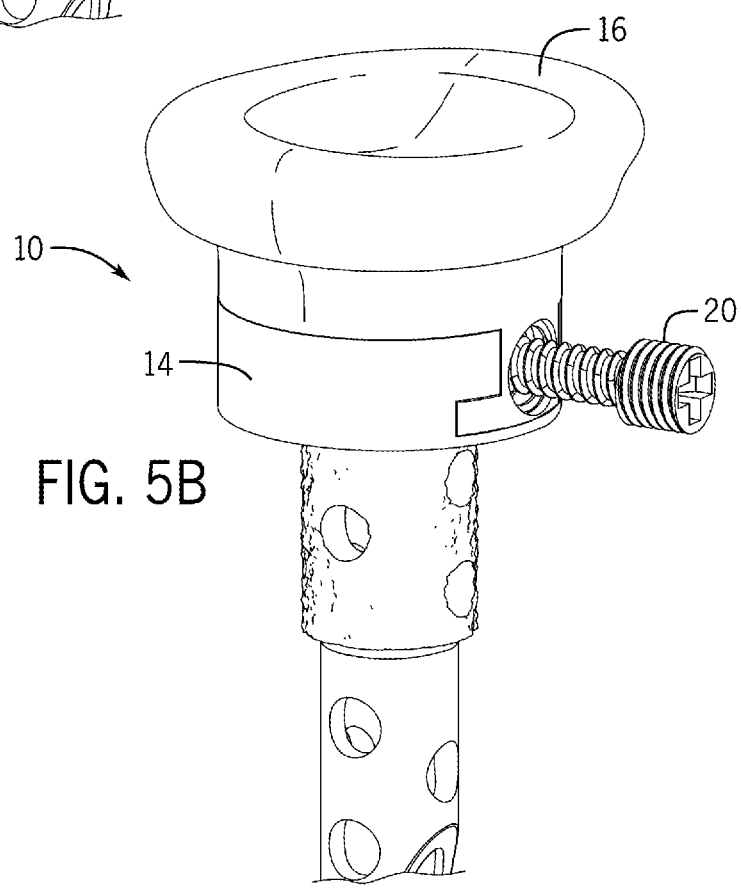
FIG. 5B illustrates an embodiment of a screw coupling the radial head component to the neck of the prosthesis.

When coupling radial head 16 to neck 14 of prosthesis 10, as shown in FIG. 5A, male protrusion 44 can be inserted into and received by female receiving cavity 32. In particular, first portion 58 of male protrusion 44 corresponds to and is received by first portion 35 of female receiving cavity 32, while shelf portion 50 of male protrusion 44 corresponds to and is received by second portion 42 of female receiving cavity 32. In this way, radial head 16 can be side-loaded into and coupled with neck 14 of prosthesis 10 by inserting male protrusion 44 of radial head 16 through sidewall opening 30 and into female receiving cavity 32. The sidewall opening 30 forms a keyed geometry with an upper first portion and a lower second portion. The lower second portion of the sidewall opening 30 extends laterally beyond a width of the upper portion of the sidewall opening 30, as shown in FIG. 5B. A total, maximum, or average width of the lower portion of the sidewall opening 30 can extend laterally around a circumference of the sidewall 28 of neck 14 to a greater degree than the upper portion of the opening 30 extends laterally around a circumference of sidewall 28 of neck 14 such that a width/lateral dimension of the lower portion of opening 30 is greater than a width/lateral dimension of the upper portion of the opening 30.

Once male protrusion 44 is at least partially inserted into and received by female receiving cavity 32, screw 20 can then be utilized to compress male protrusion 44 completely into female receiving cavity 32 and lock radial head 16 to neck 14, and therefore stem 12, of prosthesis 10, as shown in FIG. 5B.

Once compressed and locked into place, as shown in FIG. 1, the outer surface 62 of male protrusion 44 may form a flush surface with sidewall 28 of neck 14. In at least one embodiment, once male protrusion 44 is received into female receiving cavity 32 and locked such that radial head 16 is coupled to neck 14, as shown in FIG. 1, first exterior surface 46 of male protrusion 44 corresponds in position with first interior surface 34 of neck 14, second exterior surface 52 of male protrusion 44 corresponds in position with second interior surface 36 of neck 14, third exterior surface 54 of male protrusion 44 corresponds in position with third interior surface 38 of neck 14, fourth exterior surface 48 of male protrusion 44 corresponds in position with fourth interior surface 40 of neck 14, and lower surface 56 of radial head 16 corresponds in position with upper surface 26 of neck 14.

Further, in at least one embodiment, when compressed and locked as shown in FIG. 1, second interior surface 36 of neck 14 may engage second exterior surface 52 of male protrusion 44 such that second interior surface 36 of neck 14 prevents shelf portion 50 of male protrusion 44, and thus all of radial head 16, from lifting upward and out of female receiving cavity 32 of neck 14. In this way, second interior surface 36 of neck 14 can be a retaining surface contacting and/or pressing against second exterior surface 52 of male protrusion 44 to retain male protrusion 44 within female receiving cavity 32 and securing radial head 16 to neck 14.

During use, screw 20 can be tightened by engaging threads of screw 20 with complimentary threads of through-hole 60 of male protrusion 44 and hole 61 of neck 14 such that at least some of the exterior surfaces of male protrusion 44 press against at least some of the interior surfaces of neck 14. For example, when radial head 16 is coupled with and locked to neck 14 as shown in FIG. 1, at least a portion of first exterior surface 46 of male protrusion 44 is pressed against at least a portion of first interior surface 34 of neck 14. Other surfaces that correspond in position with one another, as described above, may also press against one another when radial head 16 is coupled with neck 14 of prosthesis 10.

Figure 6:
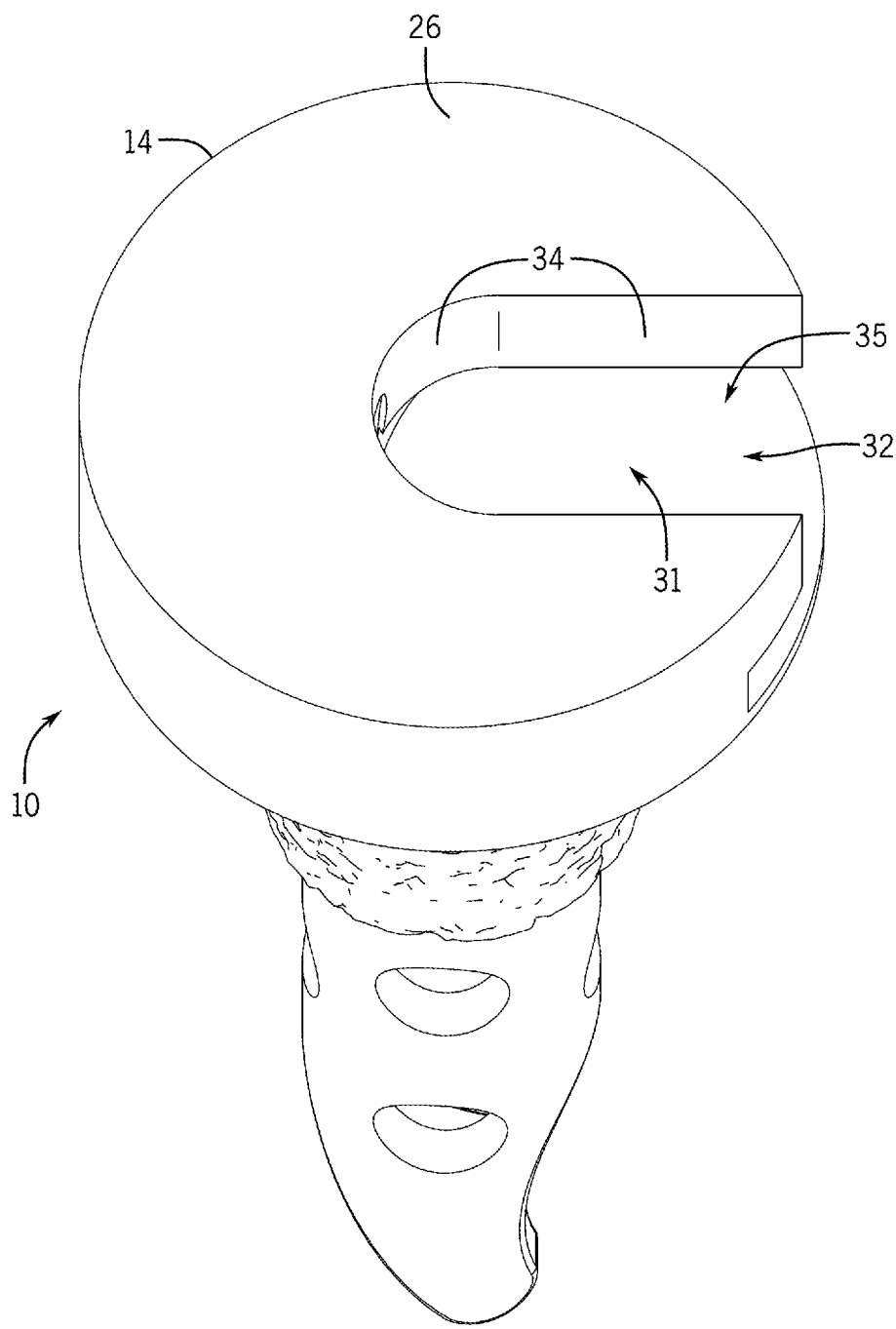
FIG. 6 illustrates a top perspective view of an embodiment of a prosthesis.

With further reference to first interior surface 34 of neck 14, as shown in FIG. 6, first interior surface 34 may extend generally downward from upper surface 26 of neck 14 defining upper surface opening 31. In at least one embodiment, opening 31, and therefore corresponding first interior surface 34, can cooperate to form a tapered channel of the first portion 35 of female receiving cavity 32, the channel having a rounded terminus. That is, straight edges of the channel of the first portion 35 of female receiving cavity 32 defined by upper surface opening 31 of neck 14 can be non-parallel to a central plane or line bisecting the channel, as shown in FIG. 6. The degree of the taper angle can vary in different embodiments, but can be about 1.49-degrees, as indicated in FIG. 6. Other embodiment may include tapers of greater or lesser degrees than 1.49, such as a taper between 1-degree and 2-degrees or tapers less than 1-degree or more than 2-degrees, for example, 2.5-degrees, 3-degrees, 4-degrees, or more than 4-degrees.

As noted above, first surface 46 of male protrusion 44 of radial head 16 can be formed or shaped to correspond with interior surface 34 of neck 14 having a similar tapered geometry and rounded terminus. In this way, when male protrusion 44 of radial head 16 is received into first portion 35 of female receiving cavity 32, a compression force from screw 20 compresses first exterior surface 46 of male protrusion 44 and first interior surface 34 of neck 14 together to form a tight, high friction compression lock between the two components and their respective surfaces. With the taper of neck 14 and taper of male protrusion 44 of radial head 16 being uniform, coupling male protrusion 44 to neck 14 forms a Morse taper. In at least one embodiment, the taper of first portion 58 of male protrusion 44 is angled at a larger degree than the taper of first portion 35 of female receiving cavity 32.

In this way, shelf portion 50 and first portion 58 of male protrusion 44 is keyed to be received and retained by second portion 42 and first portion 35 of female receiving cavity 32, respectively, through sidewall opening 30. Because male protrusion 44 is received through sidewall opening 30 in sidewall 28 of neck 14, radial head 16 can be coupled to neck 14 of prosthesis 10 without lifting or positioning top surface 22 of radial head above its final position when radial head 16 is coupled to neck 14. This can be advantageous because space above upper surface 26 of neck 14 is limited by the presence of the capitulum of the humerus bone, as well as the presence of other soft tissue such as nerves, cartilage, tendons, muscle, and the like, that surround the proximal end of the radius during radial head arthroplasty operations. Rather than risking damaging tissues such as nerves, cartilage, and adjacent bones to make room above the stem of a radial head prosthesis, so that the radial head can be inserted downward onto the stem, a surgeon can side-load the radial head 16 described herein onto the neck 14 of prosthesis 10 described herein without the need for extra space above the stem 12.

The keyed geometries of both the female receiving cavity 32 of neck 14 and the male protrusion 44 of radial head 16 can vary from one embodiment to another while allowing for the same side-load coupling. That is, the specific example of female receiving cavity 32 and male protrusion 44 shown in the FIGS. and described herein is one, non-limiting example only. Female receiving cavities and male protrusions of one or more other embodiments can include interior and exterior surfaces, openings, tapered geometries, shelf portions, other portions, and other features that differ from those shown and described herein but which provide a keyed opening defined by or through one or more side surfaces or sidewalls for receiving a keyed portion of a radial head onto the neck or stem of a prosthesis to couple the radial head to the stem from the side. However, while the size, dimensions, and shape of male protrusion 44 can vary from one embodiment to another, the embodiment of male protrusion 44 shown in the figures and described herein will be used throughout the specification as an exemplary embodiment for simplicity of explanation and illustration. Again, however, the illustrated embodiment of male protrusion 44 and the corresponding keyed geometries of the female receiving cavity 32 and sidewall opening 30 are not meant as limiting.

Figure 7A:
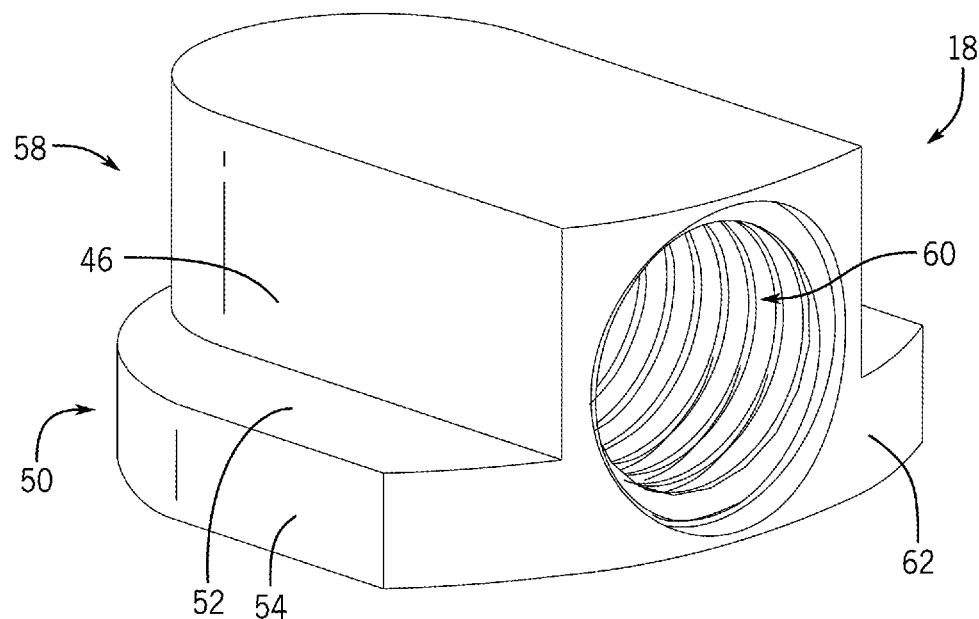
FIG. 7A illustrates a top perspective view of an embodiment of a resection cap.
Figure 7B:
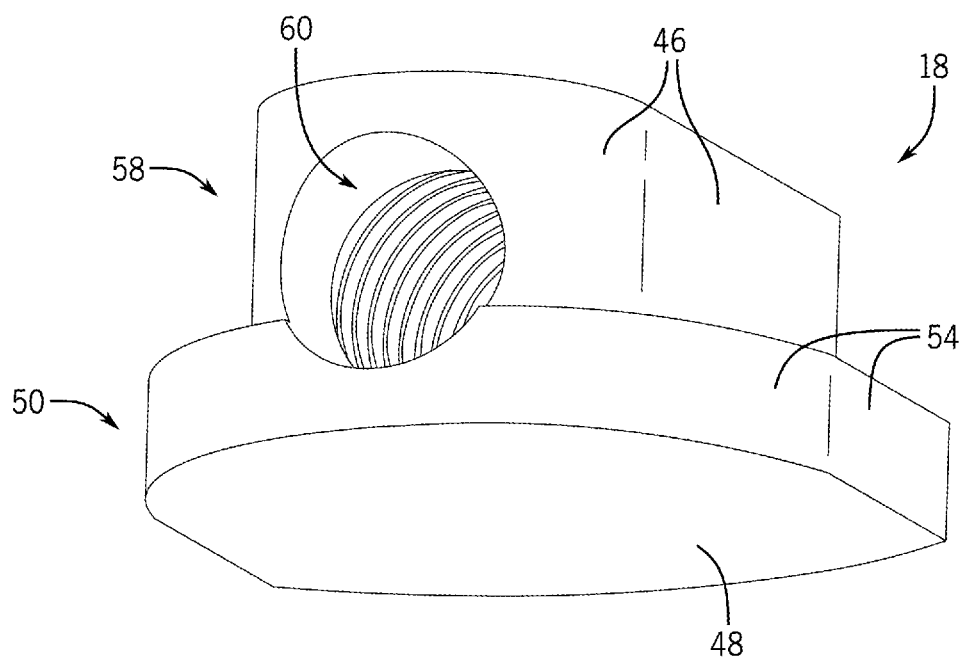
FIG. 7B illustrates a bottom perspective view of an embodiment of a resection cap.
Figure 8A:
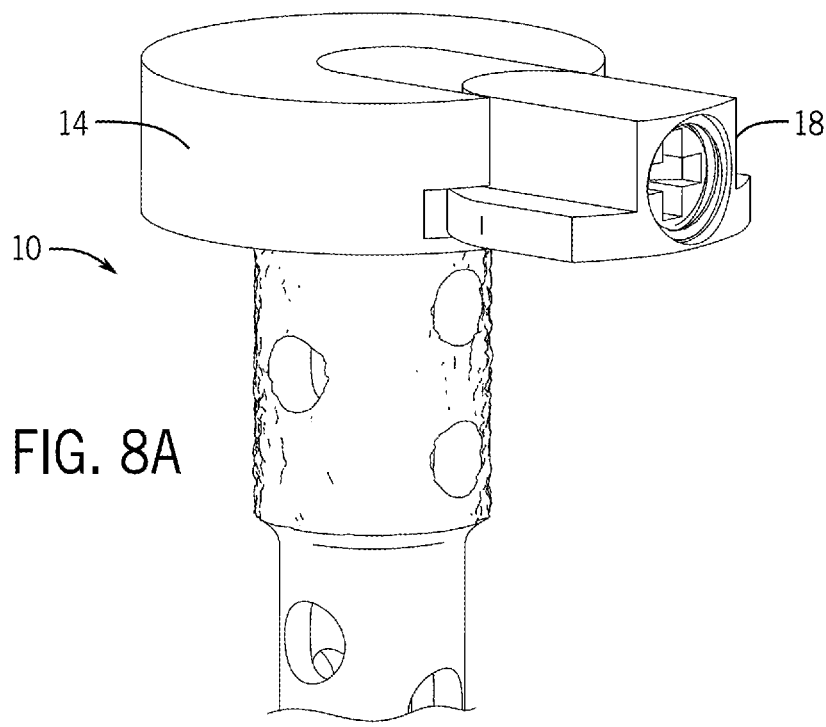
FIG. 8A illustrates an embodiment of a resection cap being inserted into the neck of a prosthesis.

One or more other components or tools of systems and devices described herein may also include male protrusions similar or different than that of male protrusion 44 shown and described with reference to FIGS. 4A, 4B, 5A, and 5B. For example, as shown in FIG. 2, a resection cap 18 can alternatively be coupled to neck 14 of prosthesis 10 similar to the way radial head 16 can be coupled to neck 14 via male protrusion 44. In at least one embodiment, for example as shown in FIGS. 7A and 7B, resection cap 18 can be shaped and sized similar to male protrusion 44 of radial head 16 shown in FIGS. 4A and 4B. As such, resection cap 18 can include first exterior surface 46, second exterior surface 52, third exterior surface 54, fourth exterior surface 48, and outer surface 62 forming first portion 58 and shelf portion 50. In this way, resection cap 18 is configured to be keyed with female receiving cavity 32 of neck 14 such that resection cap 18 can be similarly coupled to neck 14 as shown in FIG. 8A.

Figure 8B:
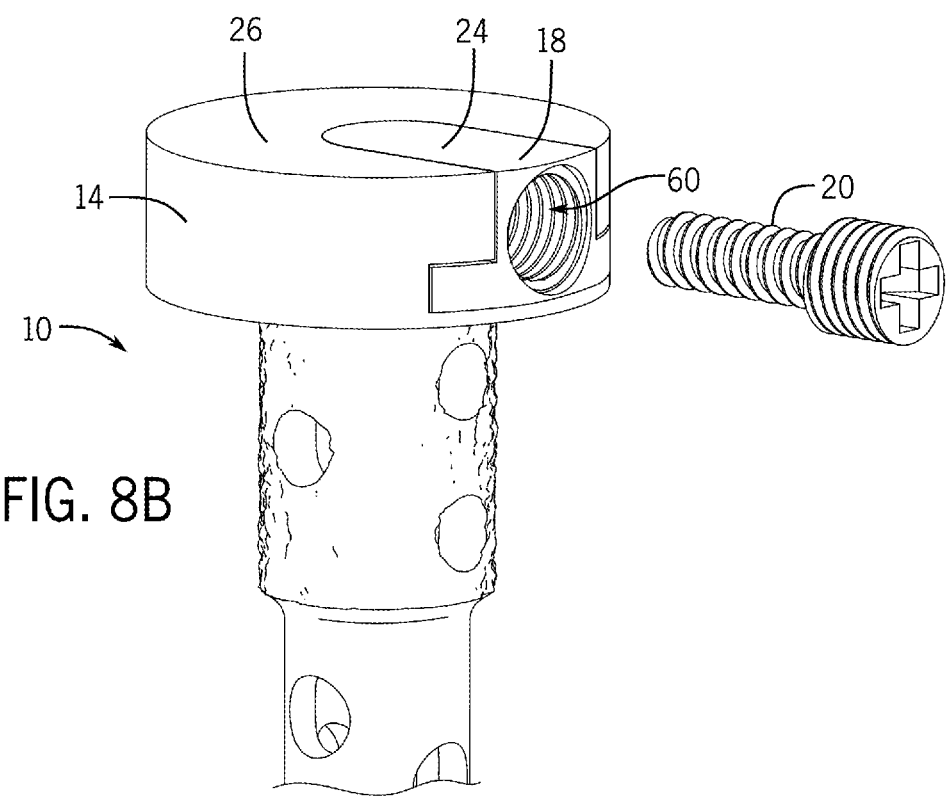
FIG. 8B illustrates an embodiment of a screw coupling the resection cap to the neck of the prosthesis.

FIGS. 7A and 7B also show a threaded through-hole 60 defined by resection cap 18. As shown in FIG. 8B, screw 20 can pass through and engage threads of through-hole 60 and hole 61 of neck 14 to compress and lock resection cap 18 to neck 14 of prosthesis 10, thus coupling them together. As noted above, and with reference to FIGS. 2 and 8B, upper surface 24 of resection cap 18 and upper surface 26 of neck 14 are generally co-planar such that the upper surface 24 of resection cap 18 does is flush with and does not extend or protrude above upper surface 26 of neck 14 when resection cap 18 is coupled to neck 14 either during or after the process of coupling resection cap 18 to neck 14 as described above.

During a resection arthroplasty procedure, radial head 16 can be removed from neck 14 by unscrewing screw 20 to decouple radial head 16 from neck 14. Once decoupled, radial head 16 can be urged sideways out from neck 14 without raising a radial head 16 upward, similar to the coupling of radial head to neck 14. Once radial head 16 is removed, resection cap 18 can be replaced in female receiving cavity 32 of neck 14 and locked in place with screw 20. Again, the insertion of resection cap 18 into neck 14 and locking resection cap 18 into neck 14 as shown in FIG. 2 results in a smooth, planar, featureless upper surface of prosthesis 10. For resection arthroplasty revision procedures using the devices and systems described herein, including resection cap 18 and prosthesis 10 having neck 14, no other portions of prosthesis 10 need be cut, removed, or otherwise altered. Again, with no additional space needed upward from or beyond upper surface 26 of neck 14 of prosthesis 10, resection 18 can be coupled as shown with minimal risk of damaging surrounding nerves, bone, cartilage, and other soft tissue.

Figure 9A:
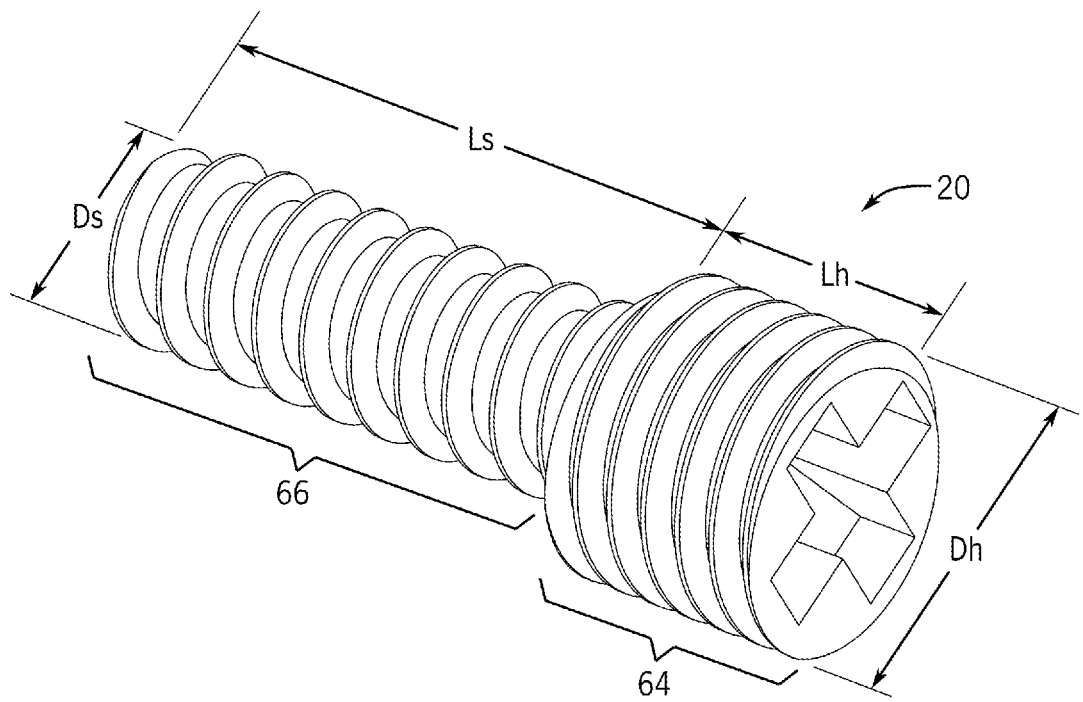
FIG. 9A illustrates a perspective view of an embodiment of a screw.
Figure 9B:
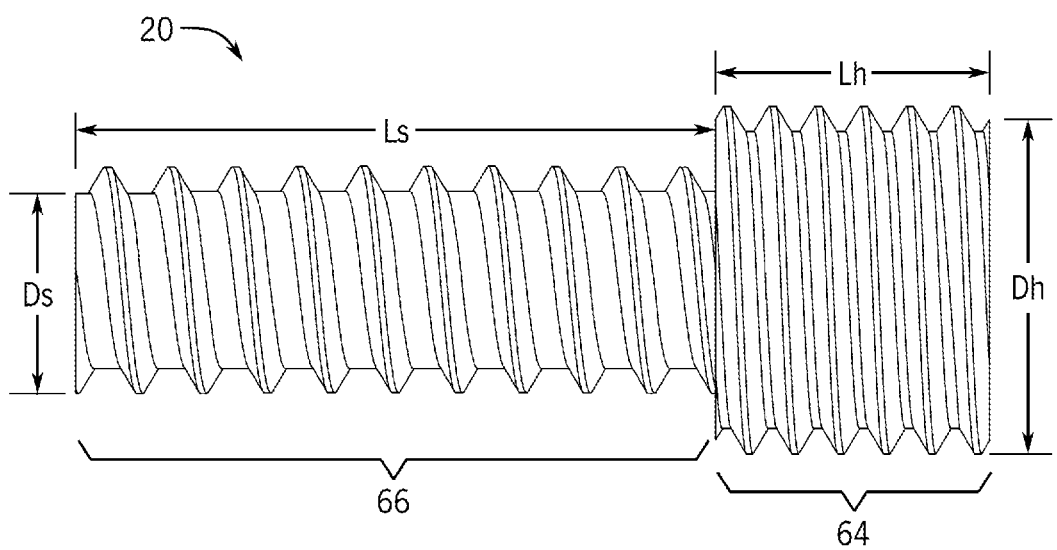
FIG. 9B illustrates a side view of an embodiment of a screw.

As noted above, screw 20 can be used to compress and lock either radial head 16 or resection cap 18 to neck 14 of prosthesis 10. FIG. 9A shows a perspective view of screw 28 in FIG. 9B shows a side view of screw 20. As shown, at least one embodiment, screw 20 includes a head 64 and a shank 66. A diameter DH of head 64 is greater than a diameter DS of shank 66. In addition, in at least one embodiment, the thread pitch of the threaded surface of head 64 differs from the thread pitch of the threaded surface of shank 66. For example, the angle of the thread pitch of head 64 may be less than the angle of the thread pitch of shank 66 such that the number of threads per unit length of head 64 is greater than the number of threads per unit length of shank 66. Head 64 is threaded to engage with internal threads of either through-hole 60 in male protrusion 44 of radial head 16 or with internal threads of through-hole 60 of resection cap 18. Shank 66 is threaded to engage internal threads of hole 61 extending into neck 14, as shown in FIG. 3. In at least one embodiment, diameter Ds and length of shank 66 is such that shank 66 passes through-hole 60 of resection cap 18 or male protrusion 44 without engaging the internal threads thereof and extends into hole 61 of neck 14 to engage the internal threads thereof.

The higher thread-per-unit-length of the threads of head 64 includes a lower pitch angle of the threads and a greater surface area of head 64. The greater surface area of head 64 is also due to the larger diameter Dh of head 64. The increased surface area of the threads of head 64 creates increased friction with the internal threads of through-hole 60 of male protrusion 44 of radial head 16 or resection cap 18 to lock radial head 16 and resection cap 18 to neck 14 of prosthesis 10. The differing thread pitches of head 64 and shank 66 allows screw 20 to compress and lock radial head 16 or resection cap 18 at the same time. A surgeon may initially or partially insert male protrusion 44 into female receiving cavity 32 manually and then fully couple them together using screw 20 until outer surface 62 of male protrusion 44 is flush with sidewall 28 of neck 14 and the two components are coupled and locked together tightly.

With threaded head 64, screw 20 can be preloaded into radial head 16 via through-hole 60 to be ready for use and set at a proper depth. With the threads on head 64 and shank 66 differing, screw 20 pulls head 64 toward neck 14 a certain distance with each rotation. The lengths of the shank and the head are critical to ensure that screw 20 does not bottom out before radial head 16 is properly secured to neck 14. With head 64 of screw 20 being threaded into through-hole 60 of male protrusion 44 of radial head 16, if radial head 16 needs to be removed, screw 20 can be reversed and push radial head 16 away from neck 14.

In one non-limiting example embodiment, screw 20 can include ISO standard M4×0.5 mm threads on head 64 and threads with 0.7 mm pitch on shank 66. In addition, a length Ls of shank 66 is about 7 mm and a length Lh of head 64 is about 3 mm and diameter Dh of head 64 is about 3.5 mm and diameter Ds of shank 66 is about 2 mm. In such an embodiment, screw 20 pulls head 64 toward neck 14 0.2 mm with each rotation. Also, in such an embodiment, full coupling of radial head 16 to neck 14 of prosthesis 10 may require 5-6 full rotations of screw 20, which means screw 20 will have engaged into hole 61 of neck 14 by between about 3.5 mm-4.2 mm and screw 20 will be sunk 2.5 mm-3 mm into through-hole 60 of male protrusion 44 of radial head 16.

Referring back to FIG. 3, prosthesis 10 includes neck 14 and stem 12 extending from neck 14. Stem 12 includes an upper textured portion 68 having a textured surface for promoting bone growth and fixation within a patient's bone. In at least one embodiment, stem 12 is hollow or at least partially hollow to define an inner volume 72. Hollow stem 12 defines a perimeter wall 74 having a thickness. As stems 12 described herein are inserted, pressed, pounded, or compacted into a patient's bone (e.g., into a reamed canal formed in a bone), the stems 12 promote press-fit fixation within a bone where a hoop-stress of the bone pressing inward on the stem 12 fixes the stem 12 and prosthesis 10 in place.

In addition, in at least one embodiment, stem 12 defines one or more apertures 70 extending from an outer surface of stem 12 to internal volume 72 through perimeter wall 74. After performing a radial head arthroplasty using prosthesis 10, the patient's bone can grow through aperture 70 to fix stem 12 within the bone. The number, size, shape, and position of each aperture 70 can vary from one embodiment to another. The amount of material removed from perimeter wall 74 of stem 12 by the number and size of apertures 70 is preferably such that the structural integrity of stem 12 is not unfit for its intended purpose and advantages described herein. On their hand, the number and size of apertures 70 is preferably such that bone growth through aperture 70, from an outside of stem 12 to inner volume 72, is promoted after prosthesis 10 is implanted. In this way, the prosthetics of the present disclosure promote bone-to-bone continuity and long-term biologic fixation of prosthesis 10.

In at least one embodiment, a distal end of stem 12 may be curved form the hooked geometry 75. The degree of curvature and the extent of stem 12 that forms hooked geometry 75 can vary from one embodiment to another. In any case, hooked geometry 75 allows the surgeon to insert stem 12 into the canal of a bone, for example a patient's radius, by angling stem 12 relative to the canal such that a distal end of stem 12 hooks into the canal. This reduces the amount of space needed above a proximal end of the radius for insertion of stem 12 into the canal and also reduces the risk of fracture in the bone when inserting stem 12.

Because the needed space proximal to the end of a patient's radius is reduced due to the curvature of stem 12, as described above, a lower ratio of the height of neck 14 and radial head 16 to the height or length of stem 12 can be achieved. That is, with hooked geometry 75 of stem 12, a longer stem 12 can be utilized to ensure sufficient compaction and long-term fixation within the bone. Ideally, for these reasons, the longer the stem the better. Accordingly, prosthetic devices and components described herein, including prosthesis 10 having hooked geometry 75 shown in FIG. 3, have a ratio or quotient (CQ) of the height of the neck 14 and radial head 16 of prosthesis 10 compared to the height or length of stem 12 of less than or equal to about 0.4.

Figure 10A:
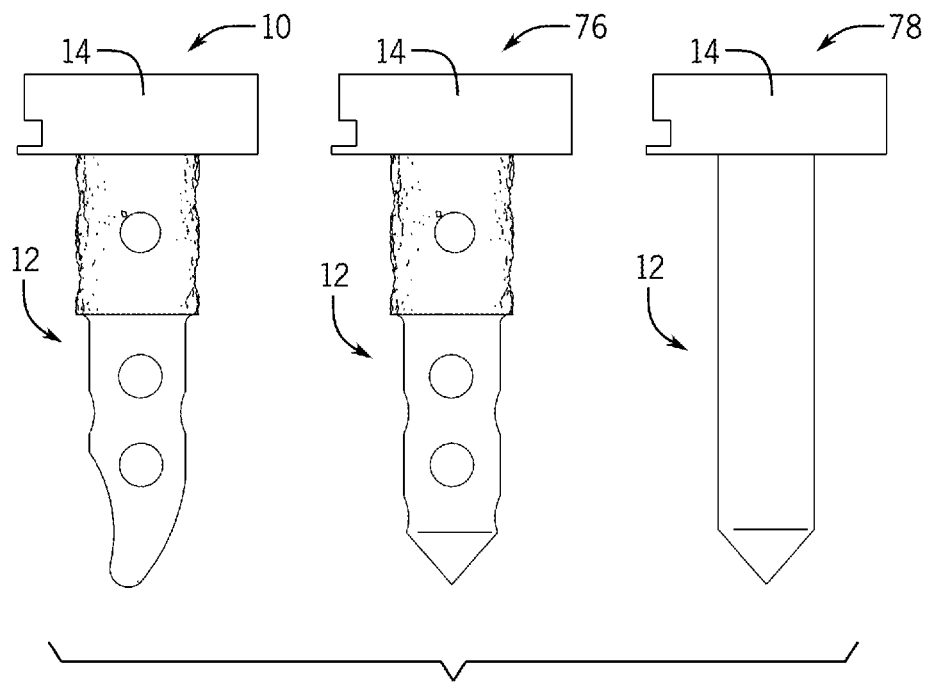
FIG. 10A illustrates side views of various embodiments of a prostheses.
Figure 10B:
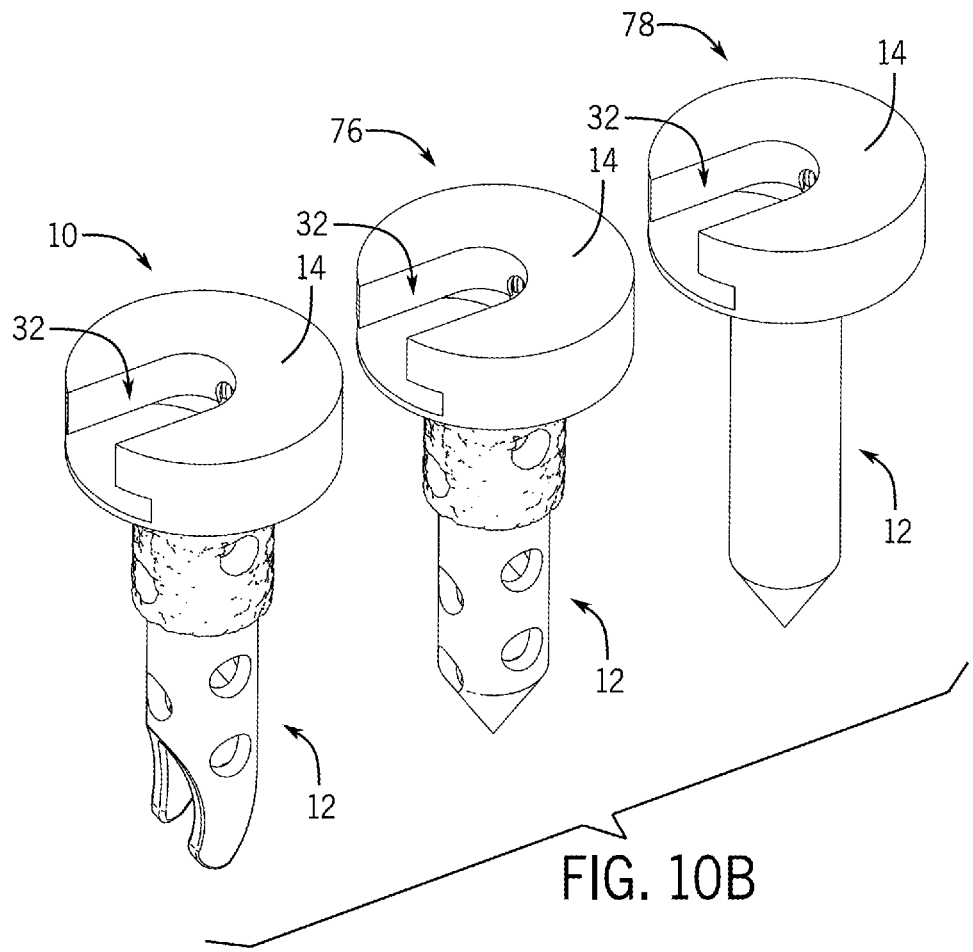
FIG. 10B illustrates top perspective views of various embodiments of prostheses.

FIGS. 10A and 10B show side views and top perspective views, respectively, of three different embodiments of prostheses. Prosthesis 10 may be similar or substantially similar to prosthesis 10 shown in FIG. 3 but with a different number, size, and arrangement of apertures. Prosthesis 76 includes a straight stem 12 without any curvature or hooked geometry. Prosthesis 78 also includes a straight stem 12 but without any apertures, textured surface portions, or curved or hooked geometries. However, in each embodiment shown in FIGS. 10A and 10B, stem 12 extends from neck 14 and neck 14 includes various interior surfaces defining female receiving cavities 32. Thus, while the features and geometries of stem 12 can vary from one embodiment to another, each stem can be coupled with a consistent neck having a consistent female receiving cavity 32 configured to receive a male protrusion 44 of radial head 16, as shown in FIG. 1. Thus, multiple stems 12 can have compatibility with multiple radial heads 16 and or resection caps 18 described herein so long as female receiving cavity 32 of neck 14 matches male protrusion portions of other the components.

Figure 11:
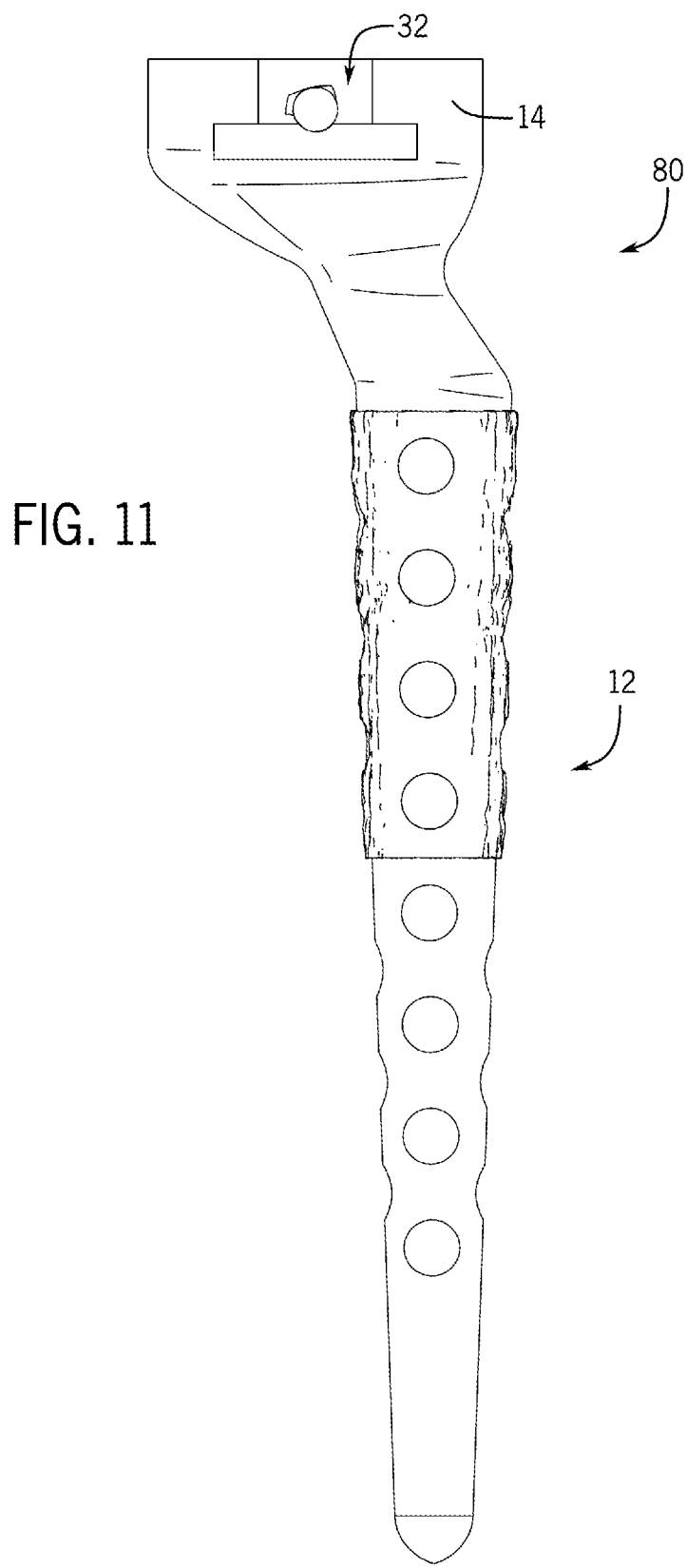
FIG. 11 illustrates a side view of an embodiment of a prosthesis.

Along these lines, FIG. 11 illustrates another embodiment of a prosthesis 80. Prosthesis 80 includes a stem 12 extending from a neck 14 but with neck 14 offset from a major longitudinal axis of stem 12. In addition, neck 14 can also include the female receiving cavity 32, similar to other prostheses described herein, where female receiving cavity 32 is shaped and sized to be keyed together with a matching, keyed male protrusion of one or more other components configured to be coupled to neck 14.

Figure 12A:
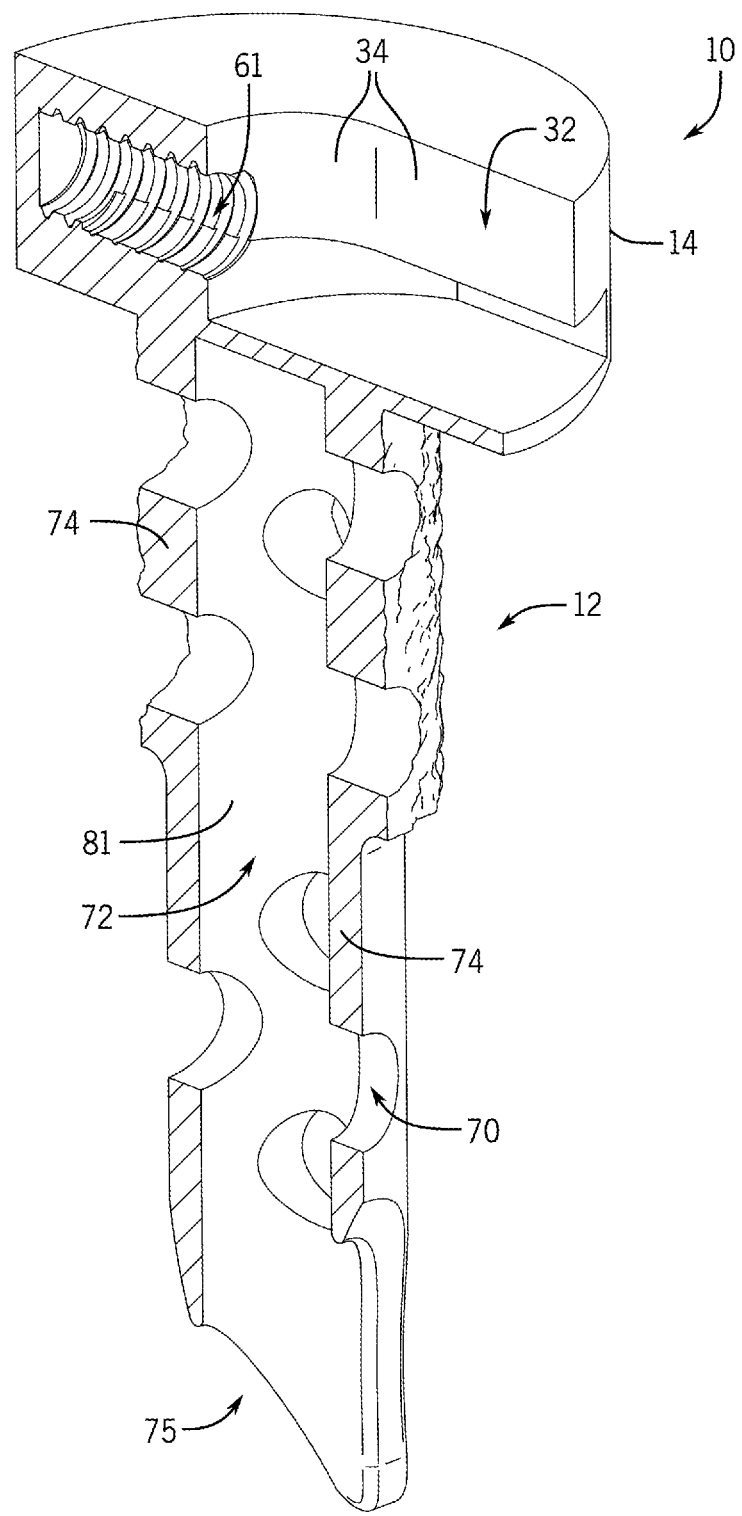
FIG. 12A illustrates a perspective cross-sectional view of an embodiment of a prosthesis.
Figure 12B:
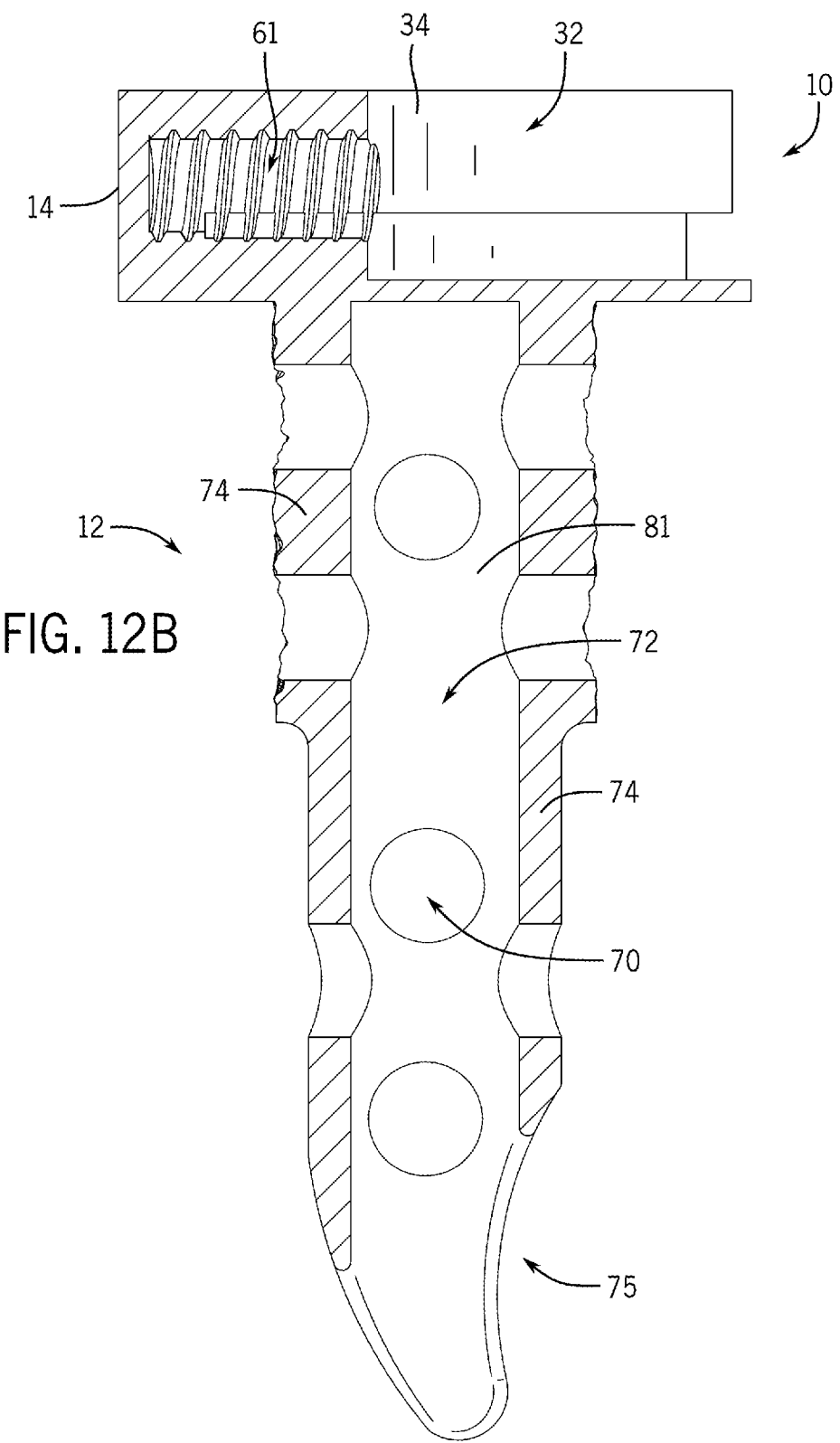
FIG. 12B illustrates a side cross-sectional view of an embodiment of a prosthesis.

FIGS. 12A and 12Be show perspective and side cross sectional views, respectively, of prosthesis 10 to illustrate inner volume 72 defined by inner surface 81 of perimeter wall 74. A thickness of perimeter wall 74 may very long the length or height of stem 12. For example, in at least one of the embodiment shown in FIGS. 12A and 12B, perimeter wall 74 is thicker at a proximal end or portion of stem 12 where an outer surface of stem 12 is textured. Perimeter wall 74 may be thinner at a distal end or distal portion and include a tapered thickness at a distal end of stem 12 where hooked geometry 75 is present.

In embodiments where stem 12 is hollow, such as the embodiment shown in FIGS. 12A and 12B, a distal end of stem 12 can be open to allow access for bone graft to be inserted into inner volume 72 in preparation for implantation of prosthesis 10. Bone graft can also be inserted into inner volume 72 through the one or more apertures 70 extending through perimeter wall 74. Bone growth can occur through apertures 70 and also through the open distal end of stem 12 to improve long-term biological fixation.

In addition to the prosthetics and associated components thereof, including radial heads 16 and resection caps 18 disclosed herein, a number of other tools, systems, and methods of use thereof can be used by surgeons to reduce the complications and difficulties associated with radial arthroplasty procedures. For example, prior to inserting a radial head prosthesis, such as those described herein, a surgeon must measure the distance between a proximal cut end of the radius and the distal end of the humerus to determine the appropriate size of the radial head prosthesis to be implemented. Typically, a surgeon may use a number of temporary trial heads, measurement blocks, or other physical gauges inserted individually to determine what size of radial head is needed. However, multiple insertions such as those commonly used in the art increases the risk of damaging surrounding tissue such as nerves, cartilage, and tendons surrounding the space between the resected neck of the proximal end of the radius and the distal end of humerus.

Figure 13:
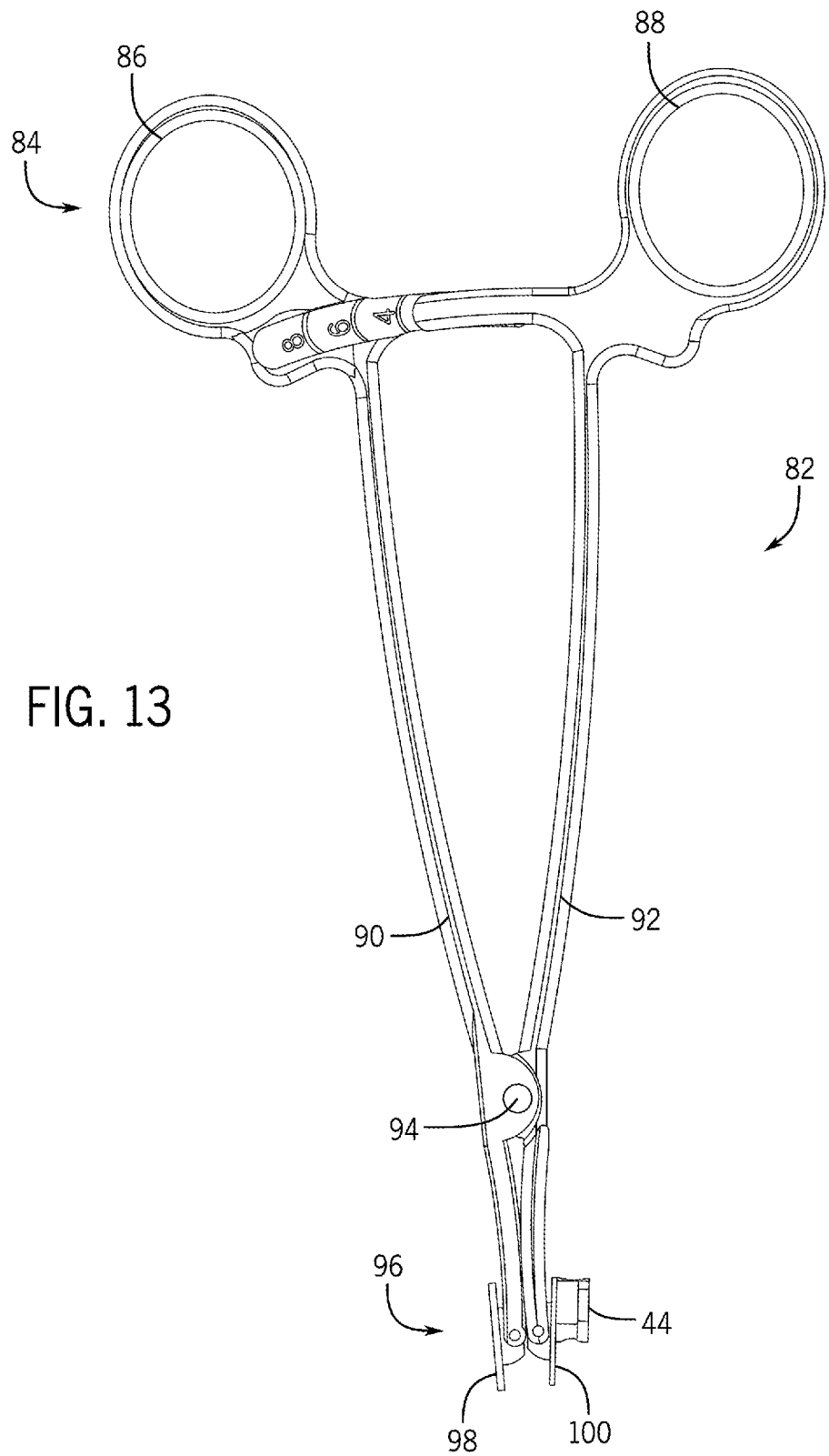
FIG. 13 illustrates a side view of an embodiment of a radial head sizing tool.

In order to simplify the measurement between the radius and humorous for determining what radial neck size is needed, a surgeon can utilize a radial head sizing tool 82, an embodiment of which is shown in FIG. 13. A proximal end 84 of sizing tool 82 includes finger grips 86 and 88 attached to an upper elongate arm 90 and a lower elongate arm 92, respectively. Upper and lower elongated arms 90, 92 are rotatably attached at hinge 94 such that moving finger grips 86, 88 closer or further away from one another causes a distal end 96 of elongate arms 90, 92 to correspondingly move closer or further away from one another.

In addition, at least one embodiment of sizing tool 82 includes an upper stop plate 98 secured to distal end 96 of upper elongate arm 90 and lower stop plate 100 secured to distal end 96 of lower elongate arm 92. Each stop plate 98, 100 can include a flat plate rotatably connected to the distal end 96 of each elongate arm 90, 92. Further, in at least one embodiment, lower stop plate 100 includes male protrusion 44 extending away from the plate 100.

Figure 14:
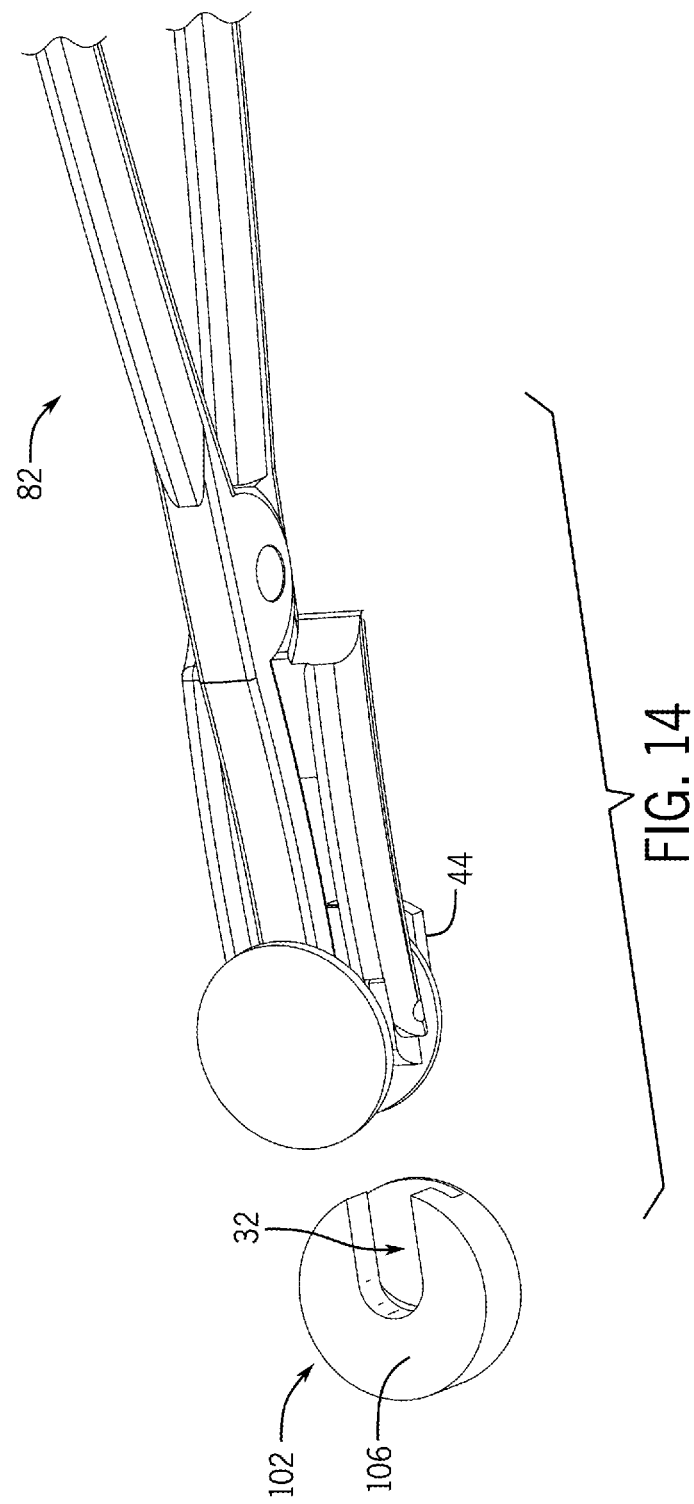
FIG. 14 illustrates a close-up view of an embodiment of a radial head sizing tool and a temporary sizing neck.
Figure 15A:
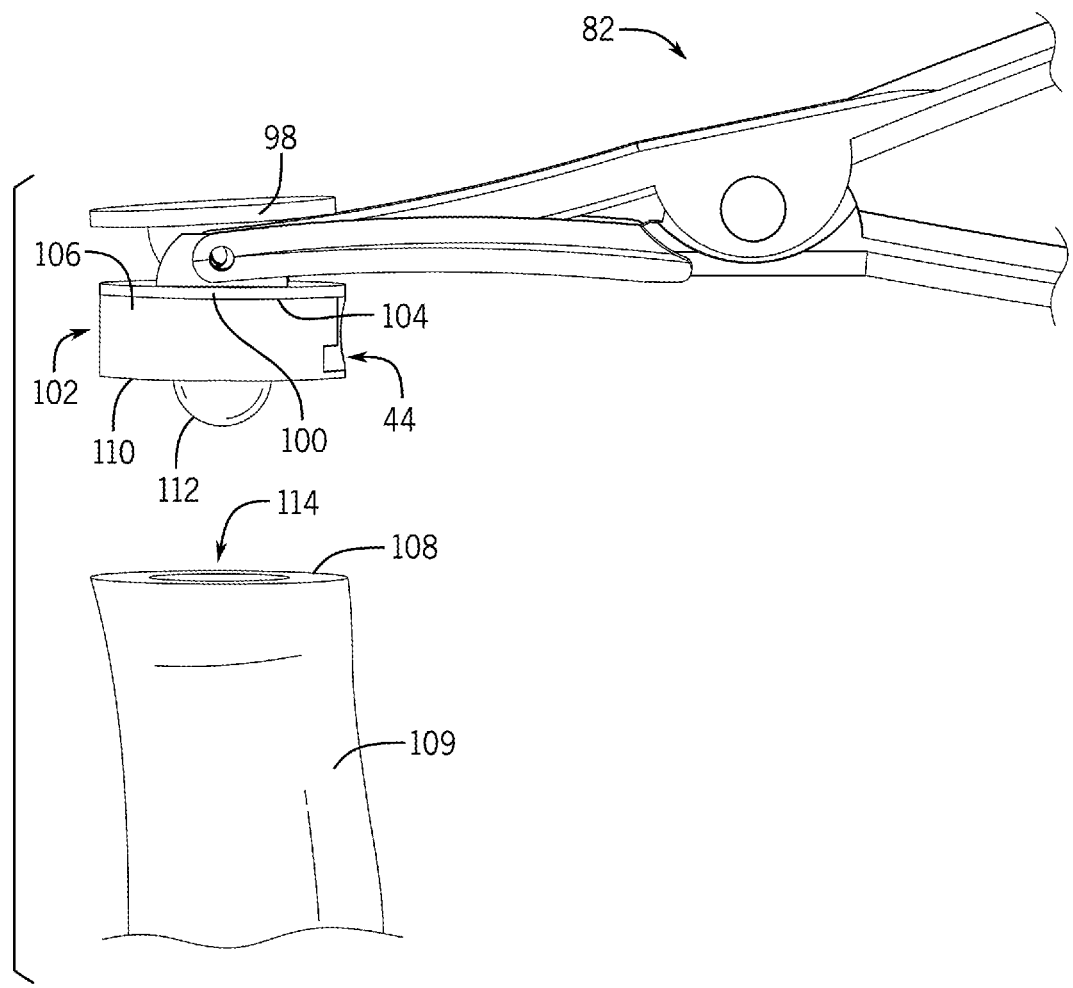
FIG. 15A illustrates a an embodiment of a radial head sizing tool interfacing with a radius bone.

Sizing tool 82 can be used in conjunction with a temporary sizing neck 102 which includes the female receiving cavity 32 configured and keyed to receive a male protrusion 44 extending from a lower stop plate 100, as shown in FIGS. 14 and 15A. FIG. 15A illustrates a side view of tool 82 and temporary sizing neck 102 coupled with lower stop surface 100 via male protrusion 44. In at least one embodiment, male protrusion 44 of tool 82 can be coupled to temporary sizing neck 102 similar to other male protrusions 44 coupled within female receiving cavities 32 of necks 14 described elsewhere herein. When coupled, a lower surface 104 of lower stop plate 100 contacts an upper surface 106 of temporary sizing neck 102. Thus coupled, tool 82 can be used to lower temporary sizing neck 102 onto a proximal cut surface 108 of a patient's radius 109 such that a lower surface 110 of temporary sizing neck 102 contacts cut surface 108. Temporary sizing neck 102 can be the same height, width, and configuration of the neck 14 of a prosthesis 10 that will ultimately be implanted. Temporary sizing neck 102 can include a shortened stem or other protrusion 112 that can be temporarily inserted into the reamed canal 114 of the radius during the measurement process.

Figure 15B:
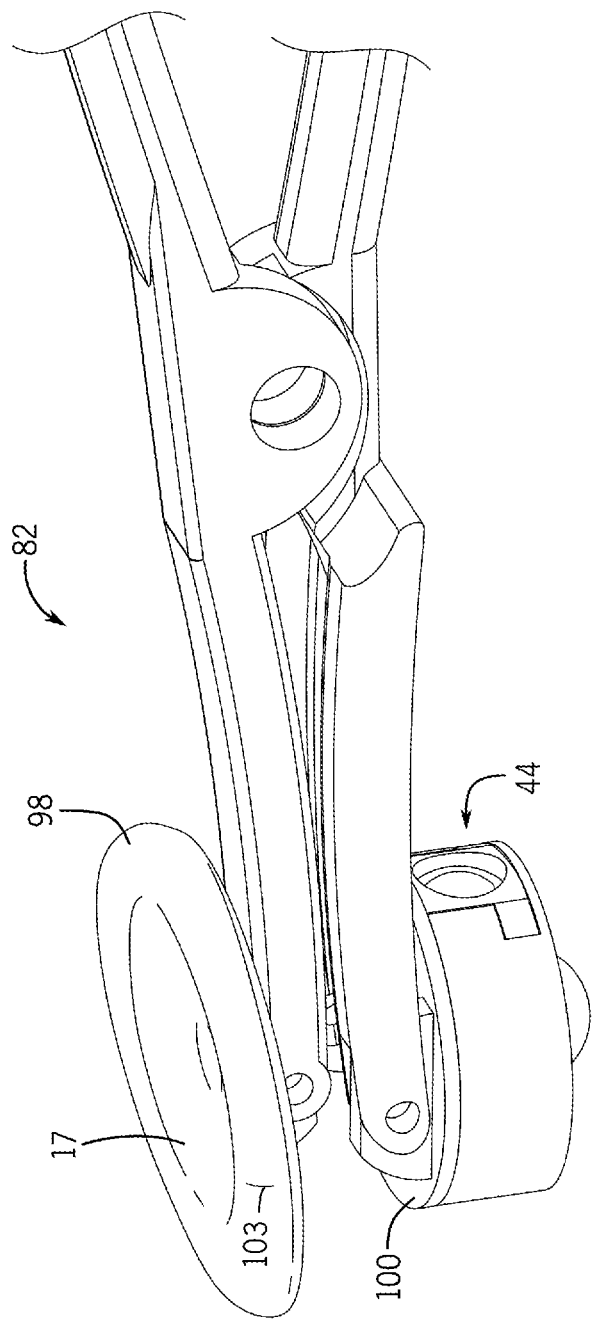
FIG. 15B illustrates an embodiment of a radial head sizing tool interfacing with a radius bone.

FIG. 15B illustrates another embodiment of a sizing tool 82, which can be used in conjunction with a temporary sizing neck 102 configured to be keyed with and receive a male protrusion 44 extending from a lower stop plate 100. The embodiment shown in FIG. 15B includes an upper stop plate 98 including or defining an upper surface 17 that is anatomically complimentary to a distal end of a humerus. Upper surface 17 of upper stop plate 98 can include a three-dimensional topography suited to match the anatomical topography of a humerus for achieving an accurate measurement with sizing tool 82. Upper stop plate 98 shown in FIG. 15B can thus be referred to as an anatomical upper stop plate 98. In at least one embodiment, the topography of upper surface 17 of anatomical upper stop plate 98 can match or be similar to an anatomical radial head that will ultimately be implanted after measurements are taken with sizing tool 82. The anatomical upper stop plate 98 can also include an alignment indicia 103 to aid the surgeon in aligning the prosthetic devices described herein. Further detail regarding the alignment indicia 103 and how it can be used to aid the surgeon is discussed in further detail below with reference to FIG. 17B. The alignment indicia 103 can include a laser etched line or other surface marking or physical feature visible to the surgeon while taking measurements with the sizing tool 82. The alignment indicia 103 can include ink marks, color variations, physical indentations or protrusions, and so forth.

Figure 16:
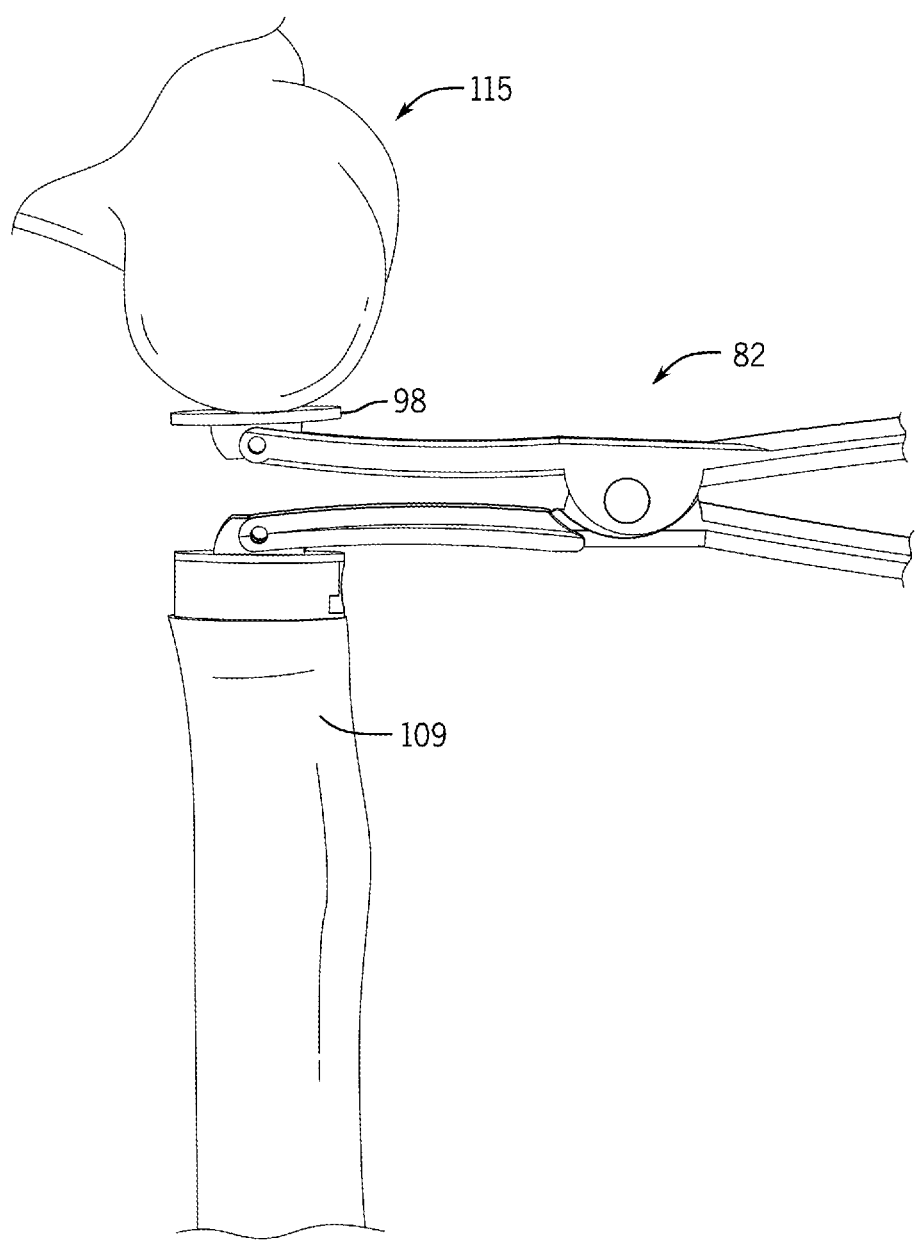
FIG. 16 illustrates an embodiment of a radial head sizing tool measuring a distance between a radius and humerus.
Figure 17A:
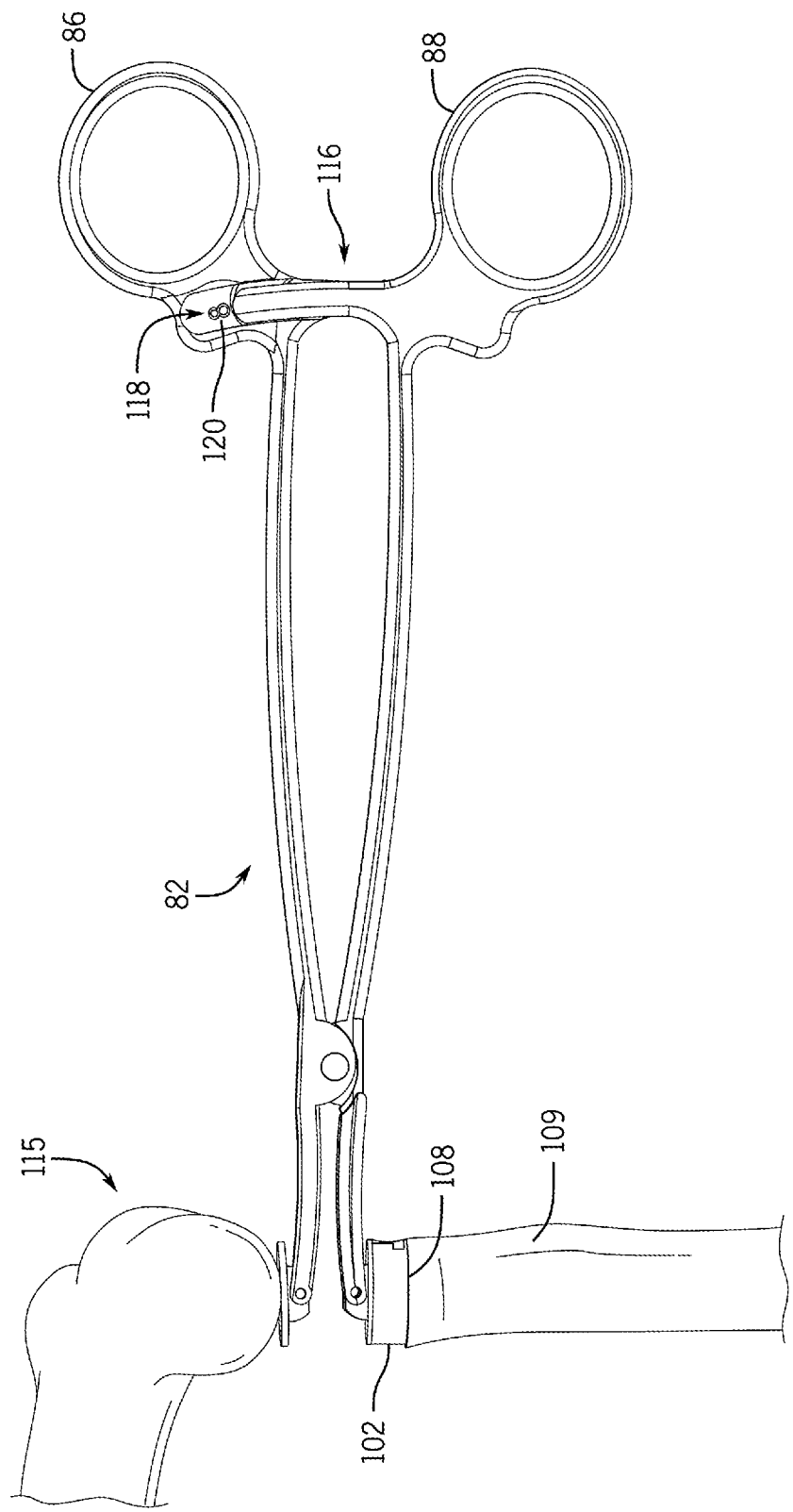
FIG. 17A illustrates an embodiment of a radial head sizing tool measuring a distance between a radius and humerus.

As shown in FIG. 16, once temporary sizing neck 102 is placed on the resected proximal end of the patient's radius 109, tool 82 can be manipulated via finger grips 86, 88 to urge upper stop plate 98 against a distal end of the patient's humerus 115. As shown in FIG. 17A, once tool 82 has positioned temporary sizing neck 102 against proximal cut surface 108 of the radius 109, a calibrated measurement indicia can indicate to the surgeon an appropriate radial neck size for a given space between proximal cut surface 108 of radius 109 and a distal end of humerus 115.

Figure 17B:
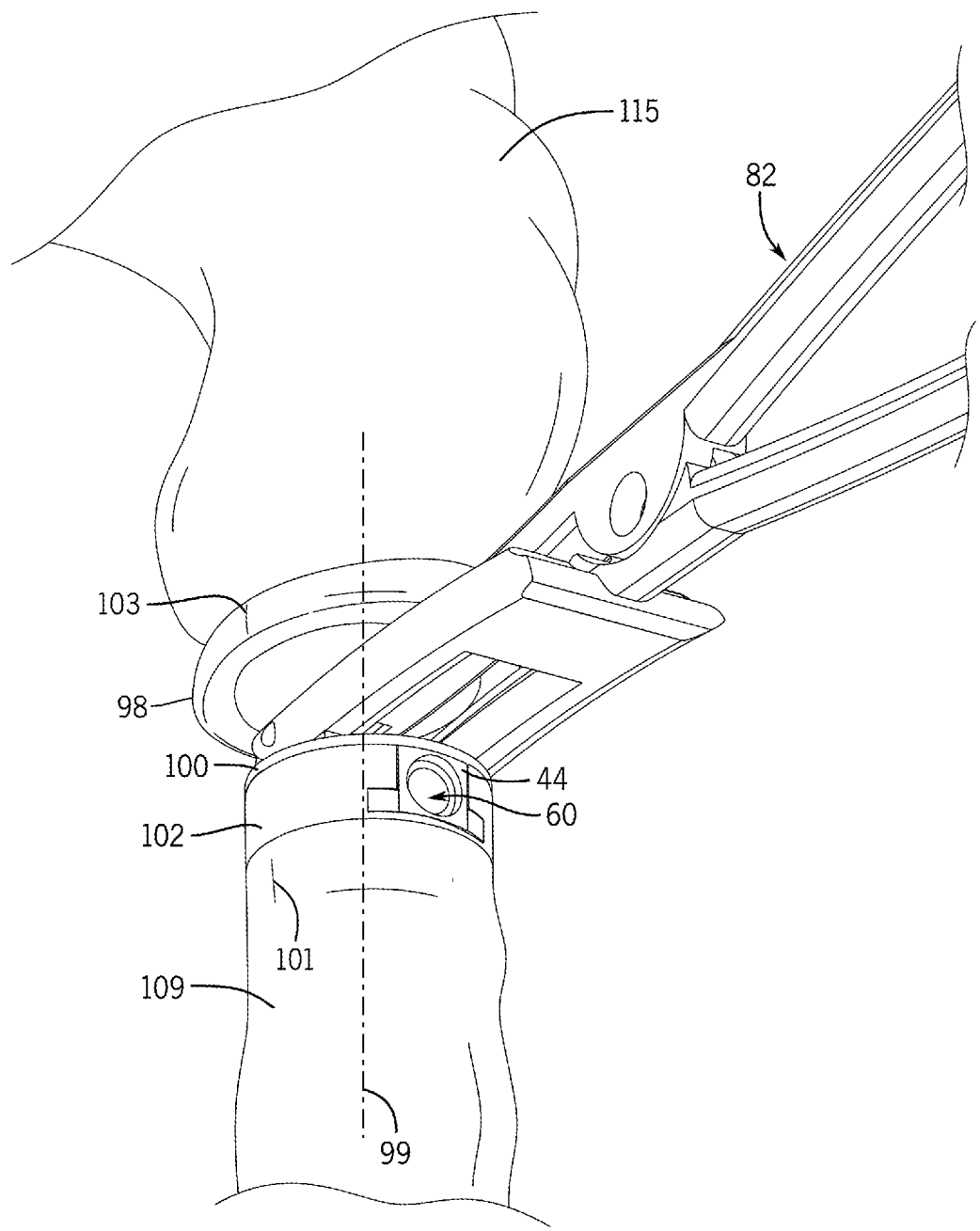
FIG. 17B illustrates an embodiment of a radial head sizing tool measuring a distance between a radius and humerus.

FIG. 17B illustrates a lower perspective view of a sizing tool 82 including an anatomical upper stop plate 98 that includes an anatomical upper surface contacting the distal end of the humerus 115. A male protrusion 44 of the lower stop plate 100, which can be engaged with temporary sizing neck 102 disposed against radius 109, can include a through-hole 60, as noted above with reference to other embodiments. After inserting upper and lower stop plates 98, 100 between the humerus 115 and radius 109 bones, and separating the upper and lower stop plates 98, 100 until upper stop plate 98 contacts the distal end of the humerus 115 and the lower stop plate 100 contacts the proximal end of the radius 109, the surgeon can rotate the sizing tool 82 such that temporary neck 102 and upper stop plate 98 rotate about a central longitudinal axis 99 of the temporary neck 102 and/or radius 109, while temporary neck 102 and upper stop plate 98 maintain contact with the radius 109 and humerus 115, respectively, until upper the upper surface of upper stop plate 98 matches well with the curvature and features of the distal end of the humerus 115.

Once the surgeon is satisfied with the positioning of anatomical upper stop plate 98 against the humerus 115, which indicates a similar position of the radial head ultimately being implanted (the radial head will or can include a upper anatomical surface matching the anatomical upper stop plate 98), the surgeon can indicate or mark a position of temporary neck relative to the radius 109. In at least one example, the surgeon can form the reference mark 101 aligned with the alignment indicia 103 of the anatomical upper stop plate 98. The reference mark 101 can include a visible marking 101 in any shape or form that indicates to the surgeon how to position the permanently implanted prosthesis after measurements are complete with the sizing tool 82, anatomical upper stop plate 98, and temporary neck 102. When the surgeon ultimately implants the prosthesis, using prostheses and devices described herein, the surgeon can align an alignment indicia of the permanent radial head, which corresponds to the same position indicated by the alignment indicia 103 of the anatomical upper stop plate 98, with the mark 101 on the radius 109 to ensure the correct orientation and positioning of the implanted prosthesis. The mark 101 can be formed in other ways, including using etching tools, inks, or other marking methods.

Figure 18:
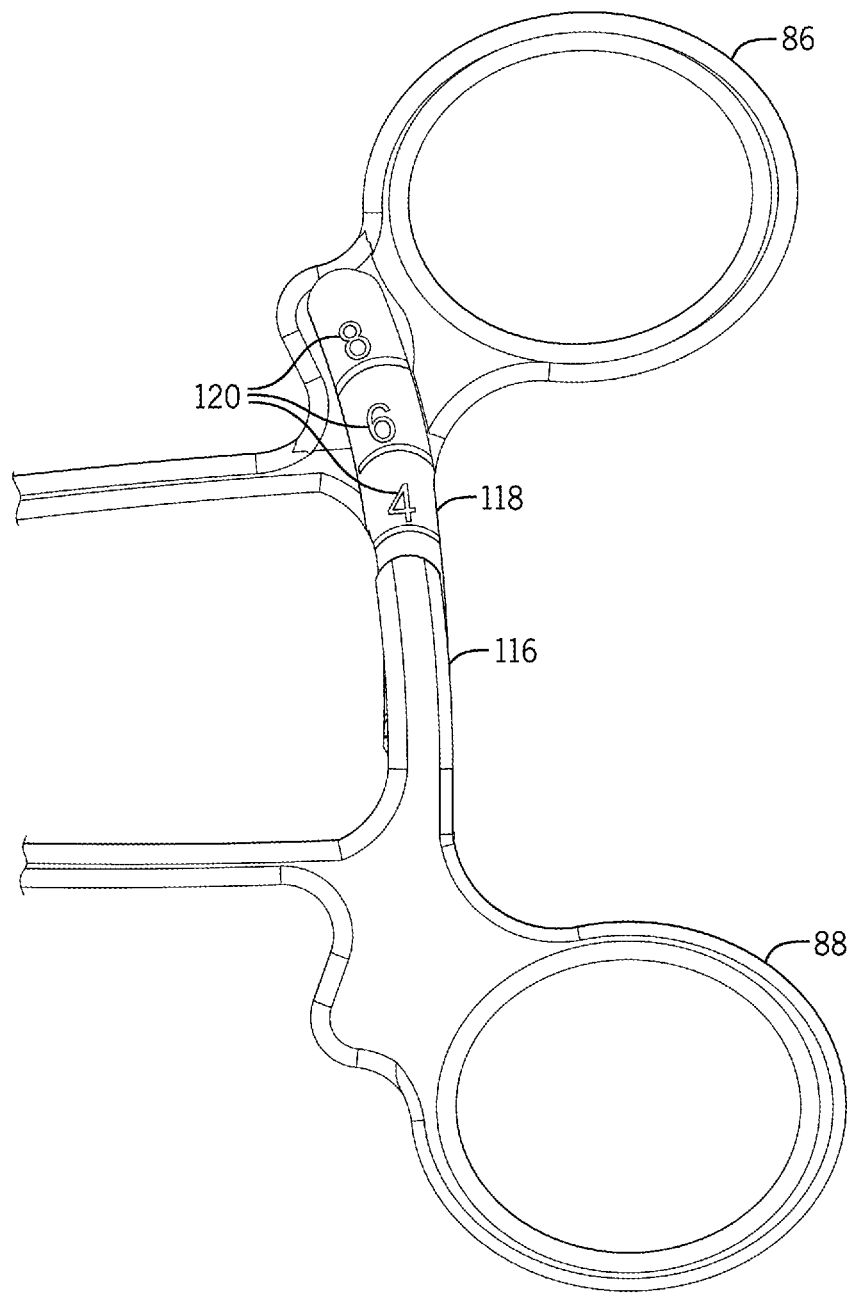
FIG. 18 illustrates a portion of an embodiment of a radial head sizing tool.

In at least one embodiment, overlapping portions 116 and 118 of finger grips 88 and 86, respectively, can reveal or indicate calibrated measurement indicia 120 corresponding to the distance between the upper stop plate 98 and lower stop plate 100. The measurement indicia 120 can corresponds to the appropriate size of a radial head that should be coupled with the prostheses described herein. FIG. 18 shows a close-up view of overlapping portions 116 and 118 and an example of various measurement indicia 120. As finger grips 86 and 88 are urged closer or further away from one another based on the distance between upper and lower stop plates 98 and 100, different measurement indicia 120 may be revealed, indicating which size of radial head is appropriate for implantation.

Figure 19:
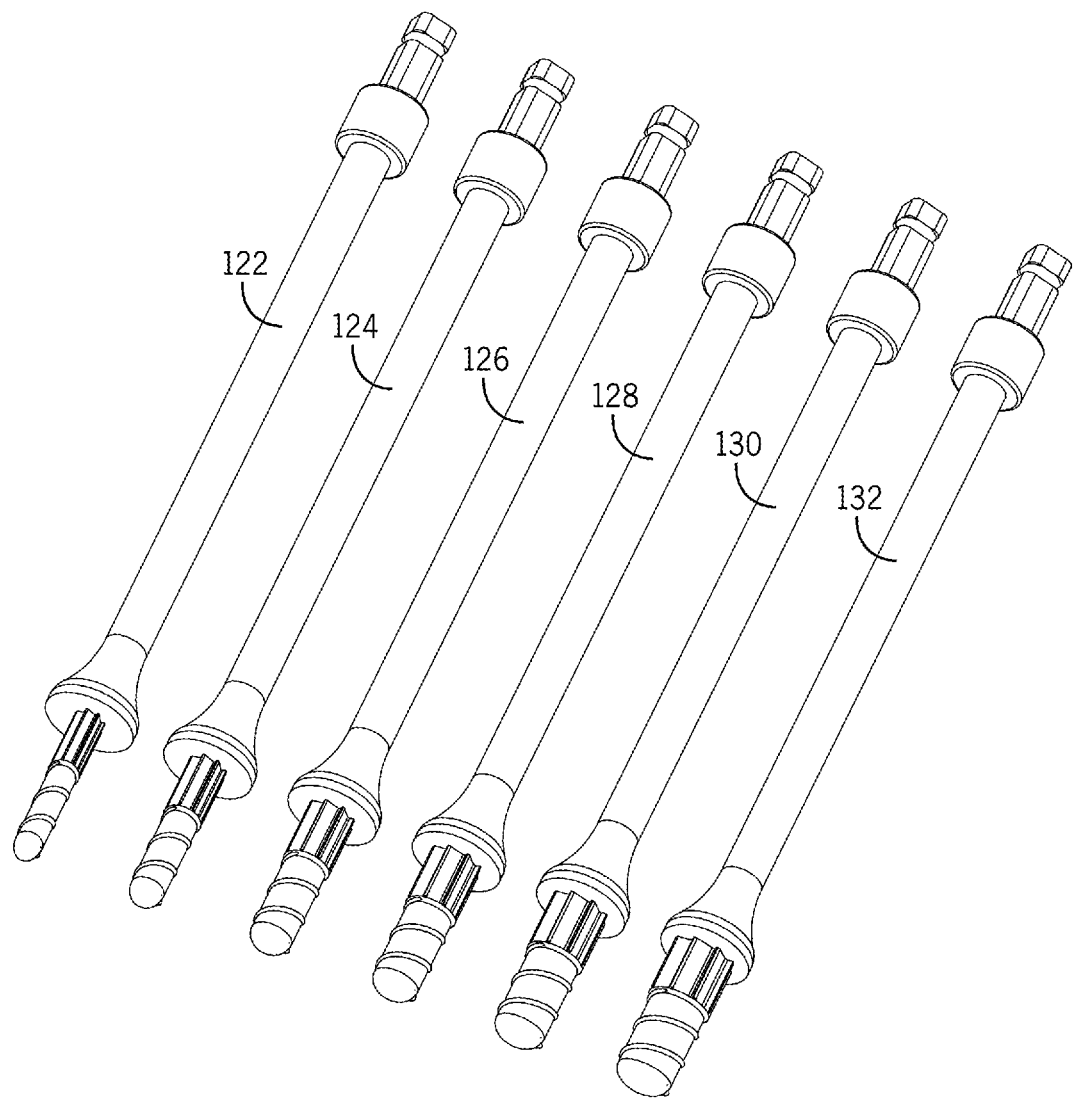
FIG. 19 illustrates a number of reamers.

One or more reamers may also be provided for surgeons to form an insertion canal in the proximal end of the patient's radius or other bone being prepared to receive the stems 12 of prostheses described herein. Along these lines, FIG. 19 illustrates a number of reamers of various sizes. Surgeons may typically start with a smaller reamer, such as a 5 mm reamer 122 and gradually expand the reamed canal of the bone with larger and larger reamers until the final canal diameter has been achieved. For example, other reamers may include a 6 mm reamer 124, a 7 mm reamer 126, an 8 mm reamer 128, a 9 mm reamer 130, a 10 mm reamer 132, and so on.

Figure 20:
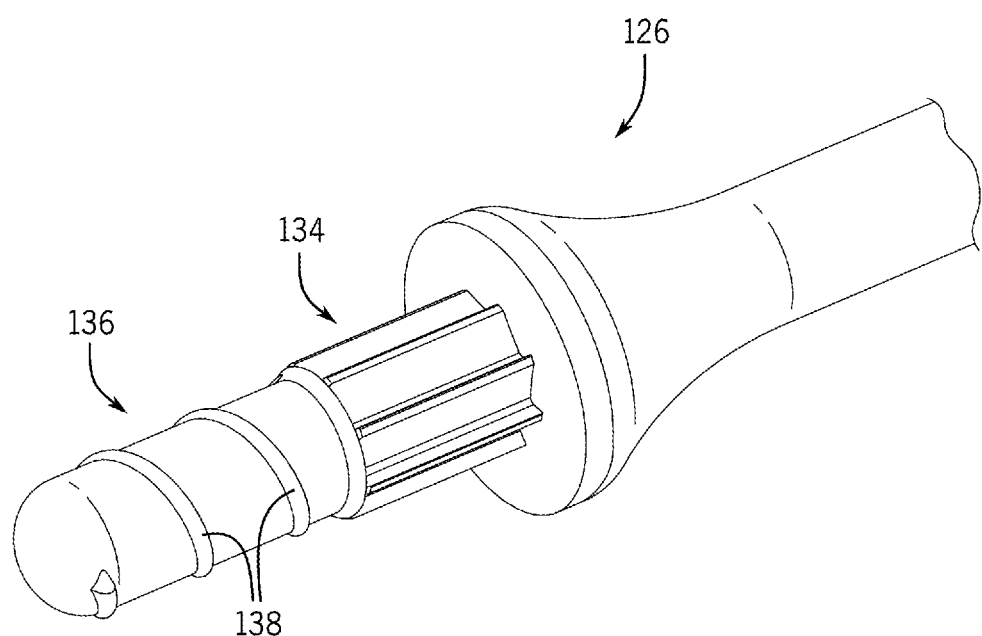
FIG. 20 illustrates a close-up view of the distal end of an embodiment of a reamer.

FIG. 20 illustrates the distal end portion of an exemplary embodiment of a reamer, such as the 7 mm reamer 126 shown in FIG. 19. The distal end portion of reamer 126 may include a proximal ribbed section 134 and a distal threaded section 136. In at least one embodiment, rather than removing bone material, the thread's 138 of the threaded section 136 can be sized and angled such that distal threaded section 136 of reamer 126 drives bone, including cancellous bone, up against the cortex of the radius instead of removing bone material. Proximal ribbed section 134 of the distal end of reamer 126 can be configured to prepare the reamed canal for the insertion of upper textured portion 68 of stem 12, as described herein and illustrated at least in FIG. 3.

During the formation of the canal, it may be advantageous to have a proximal part of the canal grow exponentially bigger based on the size of the radius while continually compressing and compacting bone distally without removing bone material that has already been compacted. This can occur as the surgeon widens or increases the size of the canal as he or she steps up the size of reamer being used. Accordingly, in at least one embodiment of reamers described herein, a diameter Dp of proximal ribbed section 134 is larger than a diameter Dd of distal threaded section 136. The ratio of these diameters diameter Dp over diameter Dd can be referred to as a reamer compaction ratio.

Figure 21:
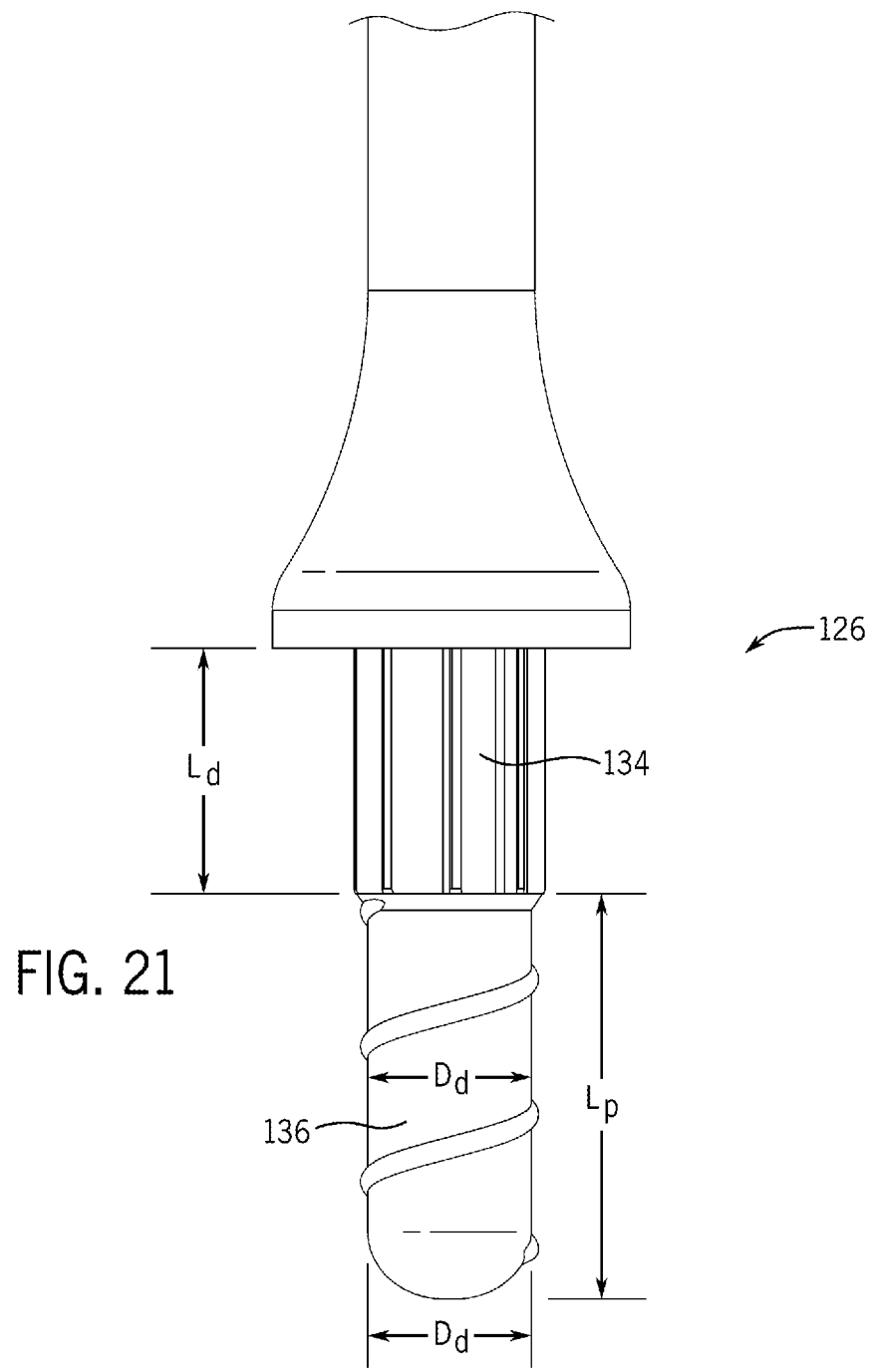
FIG. 21 illustrates a side view of the distal end of an embodiment of a reamer.

In at least one embodiment, the reamer compaction ratio increases with the size of the reamer. For example, as shown in FIG. 21, a 7 mm reamer 126 includes a distal threaded section 136 the diameter Dd of 6 mm and a proximal ribbed section 134 with a diameter Dp of 7 mm. In such an embodiment, the reamer compaction ratio is 7/6. However, the compaction ratio of a 6 mm or 5 mm reamer, or other reamer smaller than 7 mm reamer 126 shown in FIG. 21, is smaller than 7/6. Also, the compaction ratio of an 8 mm or 9 mm reamer, or other reamer larger than 7 mm reamer 126 as shown in FIG. 1, is greater than 7/6.

The length ratio of length Lp of distal threaded section 136 over length Ld of proximal ribbed section 134 may also vary, either increasing or decreasing, from one size of reamer to another. Alternatively, this length ratio may remain constant across different sizes of reamers.

Figure 22A:
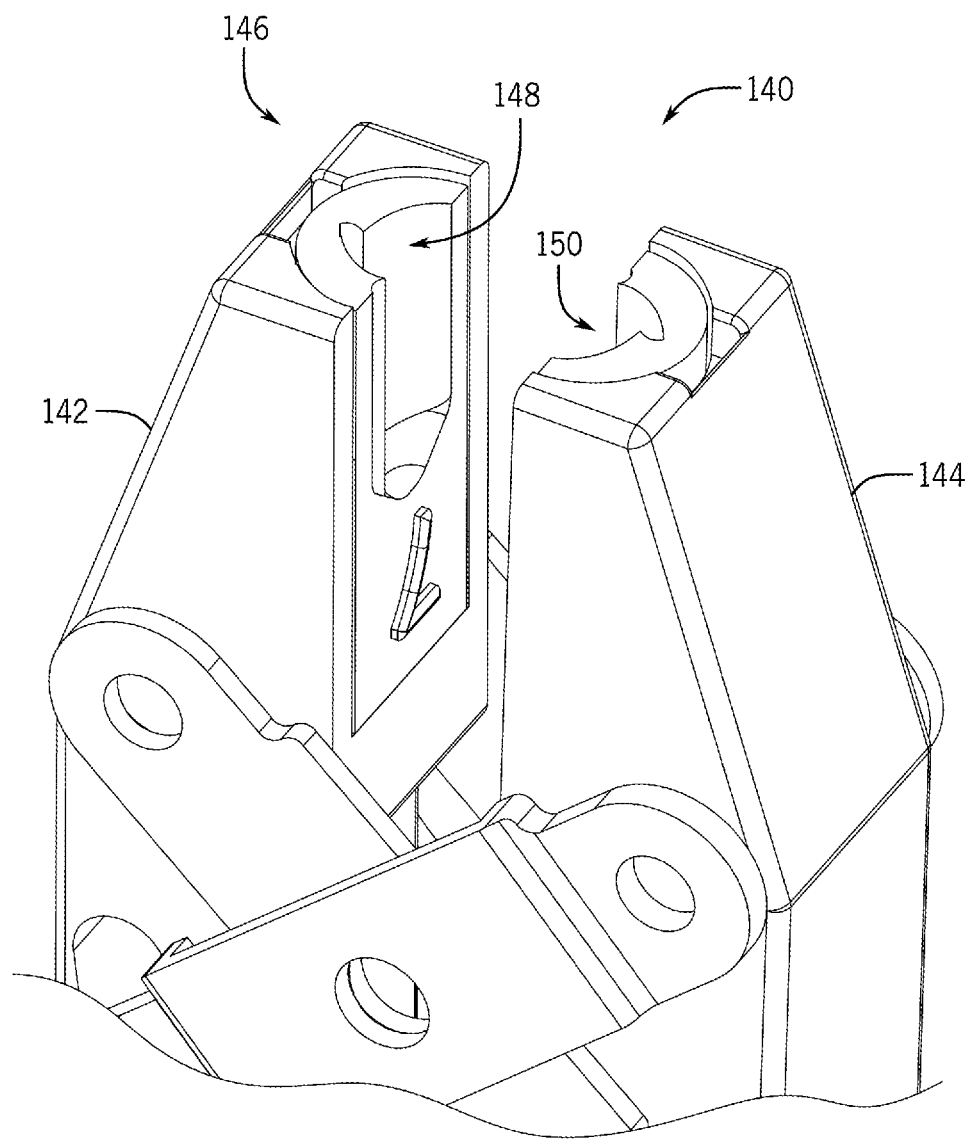
FIG. 22A illustrates a perspective view of an embodiment of a graft packer.

As noted above, prostheses described herein can be configured to receive bone graft material onto or within stem 12 in preparation for insertion into the bone canal to promote bone growth, into, through, onto, and around stem 12 for long-term biologic fixation. The more compact the graft material is on and in stem 12 of the prosthesis 10, the more compact and effective the bone on-growth will be for improved long-term fixation. In order to assist the surgeon at applying bone graft material on and in stem 12 of prosthesis 10, a graft packer 140 can be provided as shown in FIG. 22A.

Figure 22B:
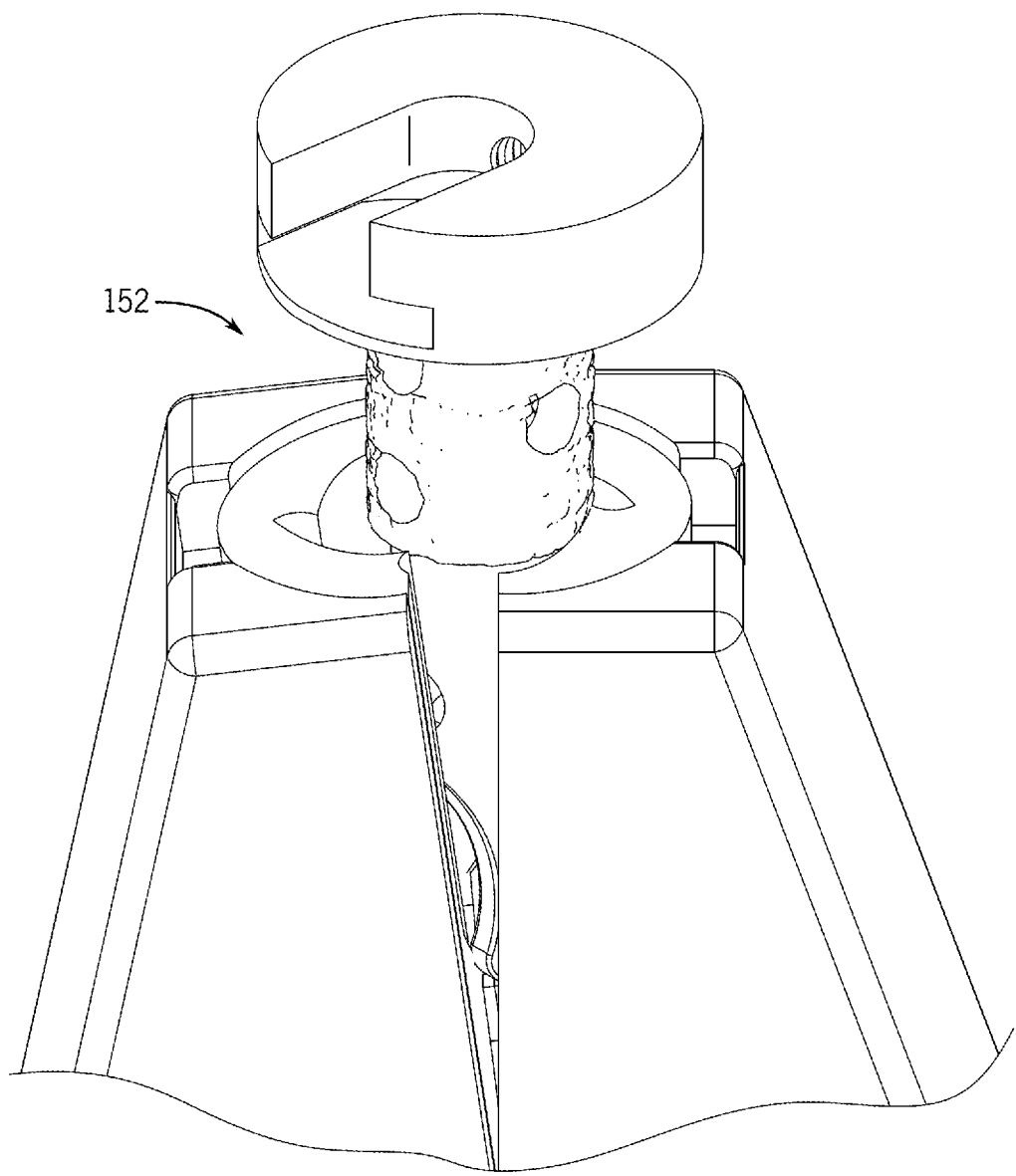
FIG. 22B illustrates a perspective view of an embodiment of a graft packer and a prosthesis inserted into a cavity of the graft packer.

At least one embodiment of graft packer 140 includes two opposing members 142 and 144 hingedly connected to one another such that a distal end 146 of graft packer 140 can be opened to receive a stem of a prosthesis. Each member 142 and 144 of graft packer 140 defines a recessed geometry 148 and 150, respectively, which form a single stem receiving cavity 152 when brought together as shown in FIG. 22B.

Figure 22C:
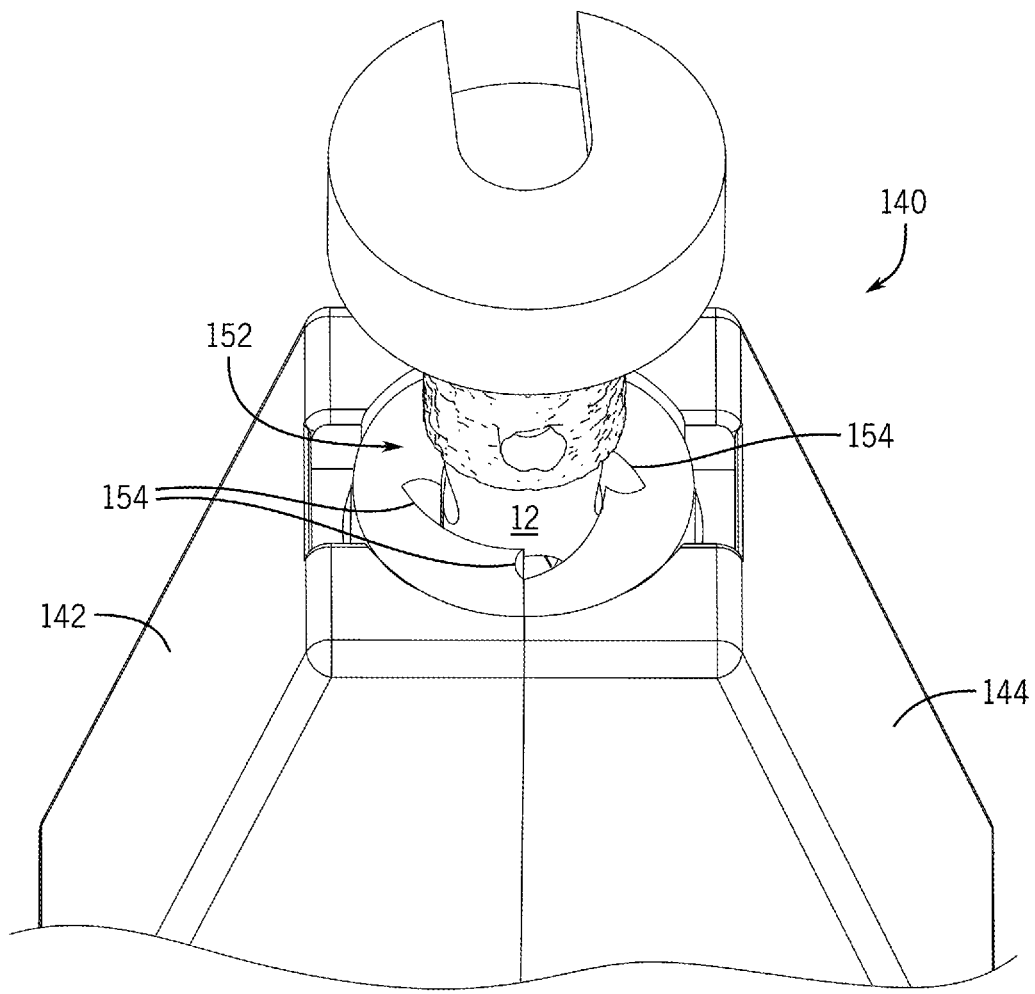
FIG. 22C illustrates a cutaway view of the graft packer showing rifled features in the cavity.

FIG. 22C illustrates an embodiment of graft packer 140 with a distal section removed to illustrate the inner surface features of stem receiving cavity 152. In at least one embodiment, various inner surfaces of recessed features 148, 150, and thus stem receiving cavity 152, cooperate to form rifled features 154 of stem receiving cavity 152, which communicate with stem 12 when inserted into stem receiving cavity 152. During use, recessed features 148 and 150 can be preloaded with bone graft material that fills or at least partially fills rifled features 154 of stem receiving cavity 152. When members 142 one 144 are clamped together against stem 12 as shown in FIG. 22C, stem 12 can be rotated to pack bone graft material disposed within stem receiving cavity 152 and rifled features 154 into the apertures, inner volume, and onto the outer surface of stem 12.

Figure 23:
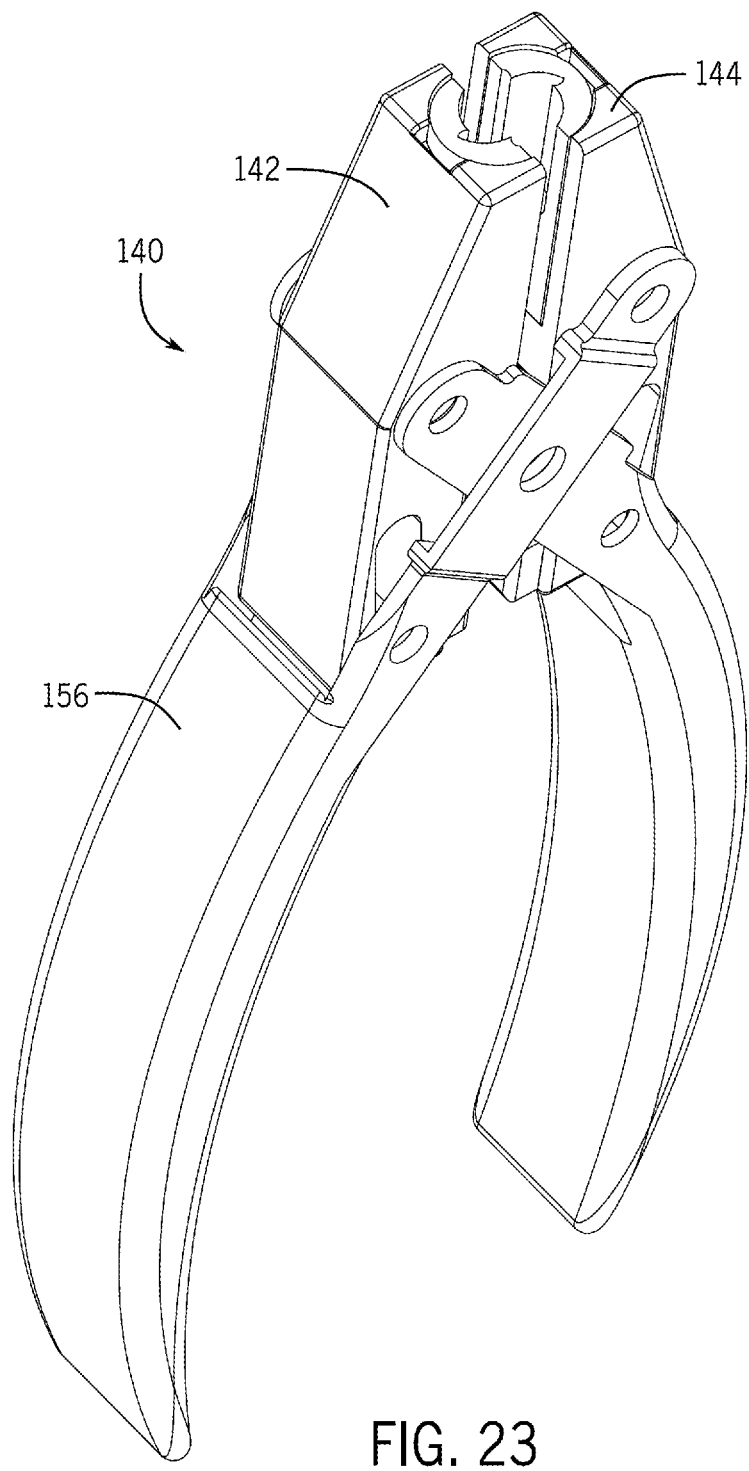
FIG. 23 illustrates an embodiment of a graft packer manual clamp mechanism.

FIG. 23 illustrates another embodiment of graft packer 140 including a manual clamp mechanism 156 secured to members 142 and 144. Manual clamp mechanism 156 can be secured to members 142 and 144 in such a way that the surgeon can manually grasp clamp mechanism 156 to urge members 142 and 144 together to form stem receiving cavity 152.

Figure 24:
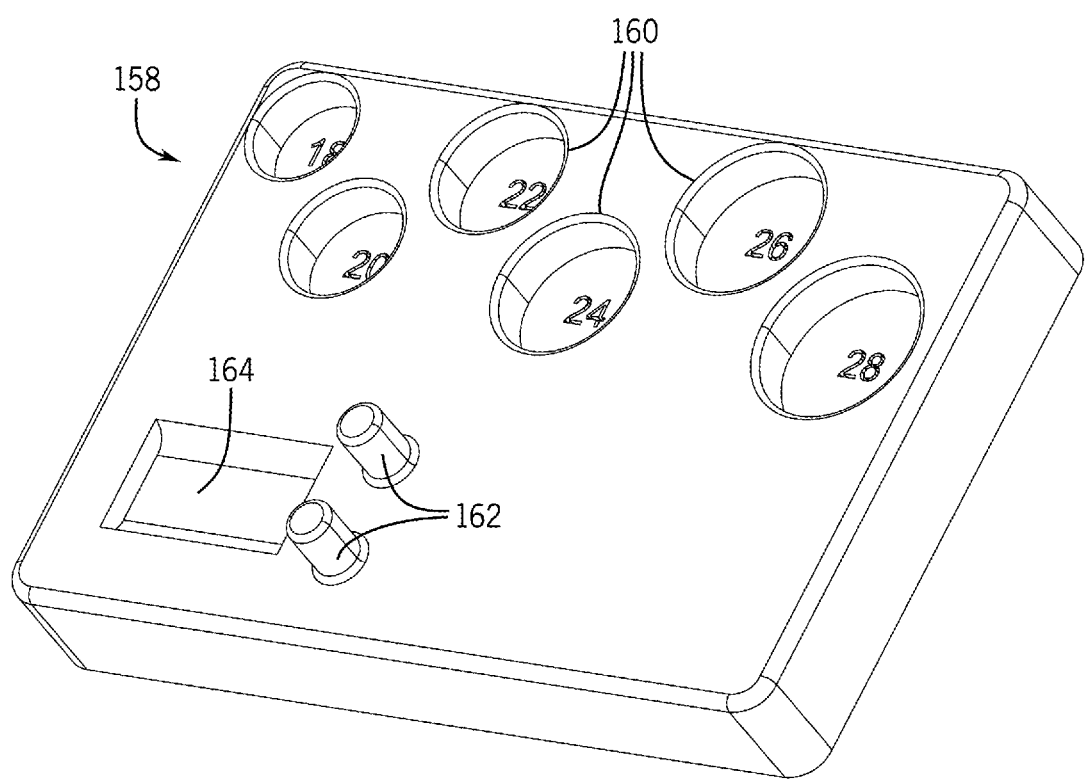
FIG. 24 illustrates a perspective view of an embodiment of a sizing block.

A surgeon can also utilize a resected radial head sizing block, such as sizing block 158 shown in FIG. 24, during or before radial head arthroplasty procedures. At least one embodiment of sizing block 158 includes a number of sizing recesses 160 of varying sizes. Once the damaged radial head of the patient's radius is resected, the surgeon can place the resected head into the sizing recesses 160 to determine the size of the resected head. Each sizing recess 160 can be labeled with a corresponding radial head implant size so that the surgeon knows what size of radial head to implant.

Figure 25A:
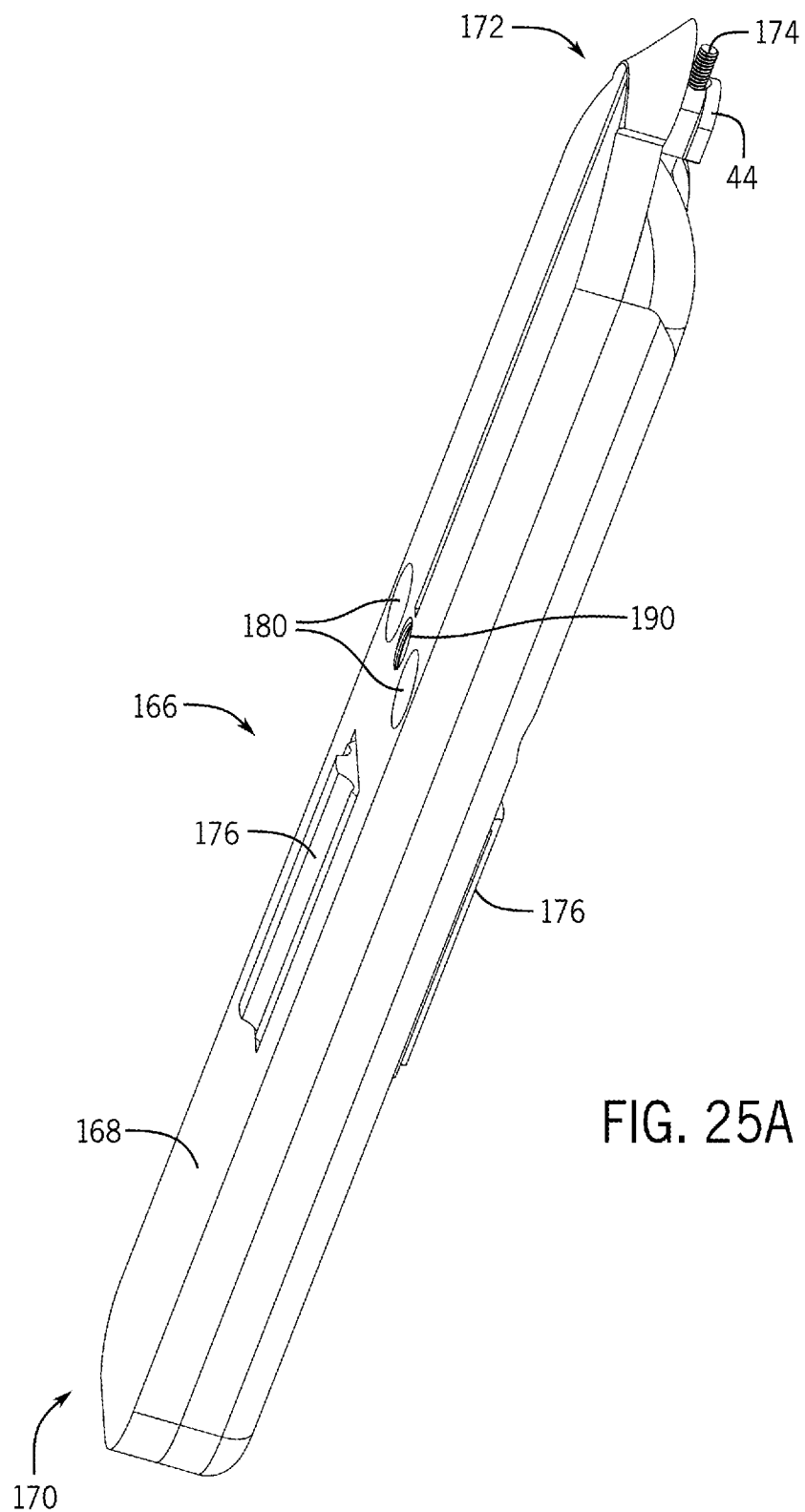
FIG. 25A illustrates a perspective view of an embodiment of a stem insertion handle.

In addition, at least one embodiment of sizing block 158 includes one or more fixation features 162 and recessed portion 164. Fixation features 162 and recessed portion 164 can be configured to receive and secure a stem insertion handle. An embodiment of a stent insertion handle 166 is shown in FIG. 25A. Stem insertion handle 166 can include the main body 168 having a proximal end 170 and a distal end 172. In addition, at least one embodiment of stem insertion handle 166 includes a male protrusion 44 extending from a distal end 172 of the main body 168. Male protrusion 44 can be configured to be received into a female receiving cavity 32 of a neck 14 of prosthesis 10 to couple stem insertion handle 166 to prosthesis 10. To lock male protrusion 44 of stem insertion handle 166 to neck 14 of prosthesis 10, screw 174, which extends distally from male protrusion 44 can be rotated via screw mechanism 176.

Figure 25B:
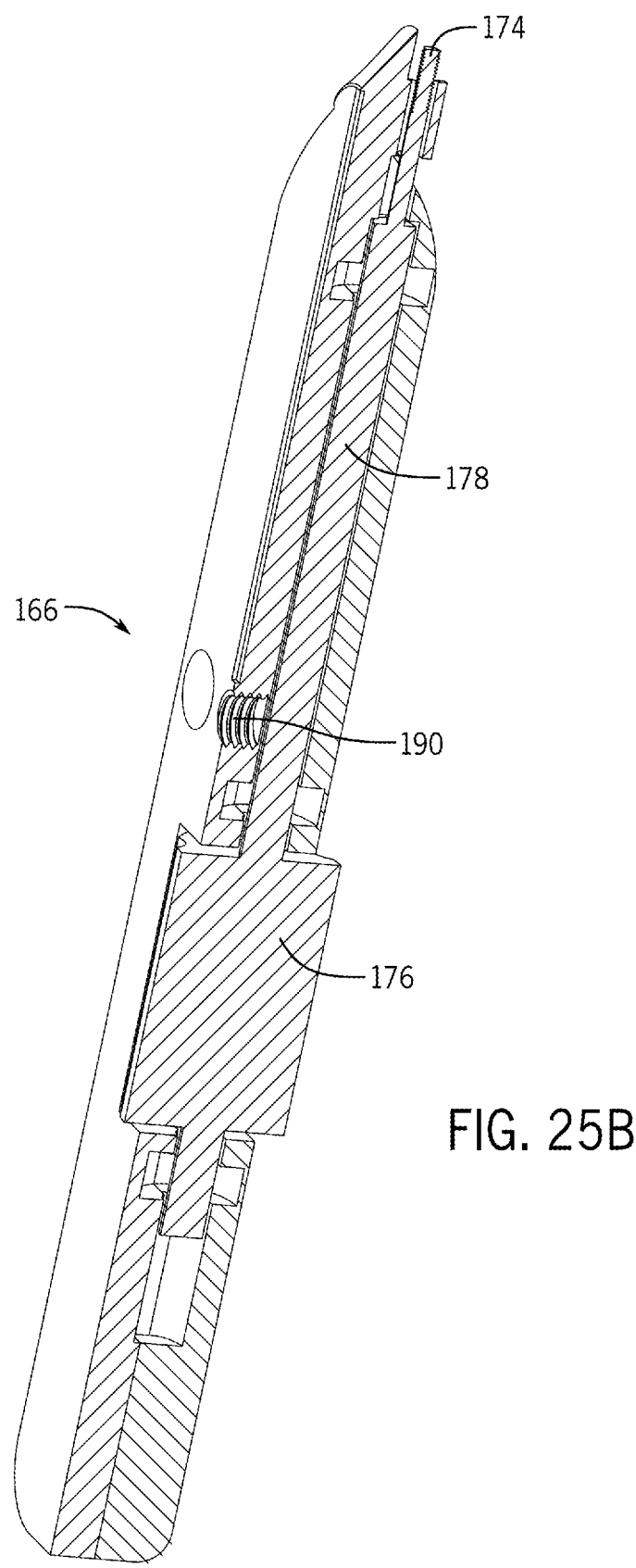
FIG. 25B illustrates a perspective cross-sectional view of an embodiment of a stem insertion handle.

In at least one embodiment, screw mechanism 176 extends above and below main body 168 so that a surgeon attaching a prosthesis to stem insertion handle 166 can grip and rotate screw mechanism 176 to rotate screw 174. As shown in FIG. 25B, screw mechanism 176 is coupled to or includes elongate member 178, which is coupled to screw 174. As the surgeon rotates screw mechanism 176, screw 174 is thus also rotated. In this way, a surgeon can insert screw 174 into hole 61 of neck 14 of a prosthesis, such as prosthesis 10 described herein, to secure prosthesis 10 to stem insertion handle 166.

Referring back to FIG. 25A, at least one embodiment of the stem insertion handle 166 includes one or more through-holes 180. Through-holes 180 can be sized and positioned through main body 168 of stem insertion handle 166 such that fixation features 162 of sizing block 158 extend into or through a through-holes 180 to couple stem insertion handle 166 to sizing block 158. In addition, the portion of screw mechanism 176 that extends below main body 168 of stem insertion handle 166 may extend into recessed portion 164 of sizing block 158 so that main body 168 of stem insertion handle 166 can rest flush against a top surface of sizing block 158 during use.

Figure 26:
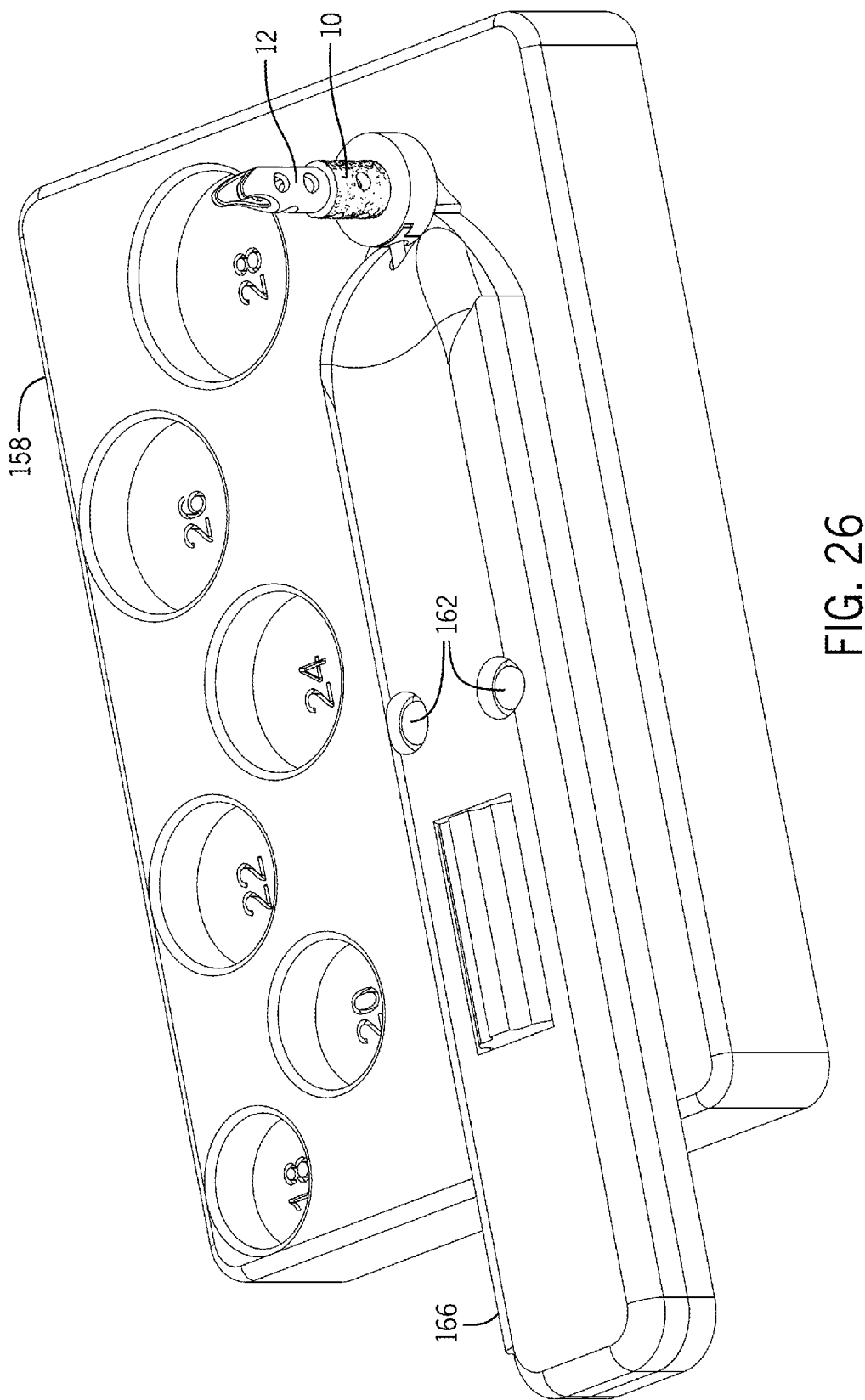
FIG. 26 illustrates a perspective view of a stem insertion handle coupled to an embodiment of a sizing block.

FIG. 26 illustrates stem insertion handle 166 coupled to sizing block 158 with prosthesis 10 coupled to stem insertion handle 166. The surgeon can pack bone graft material onto or into stem 12 of prosthesis 10 using tools and methods described herein while stem insertion handle 166 is coupled to sizing block 158. In this way, the surgeon can avoid dropping or damaging prosthesis 10 during preparation for radial head arthroplasty procedures.

Figure 27:
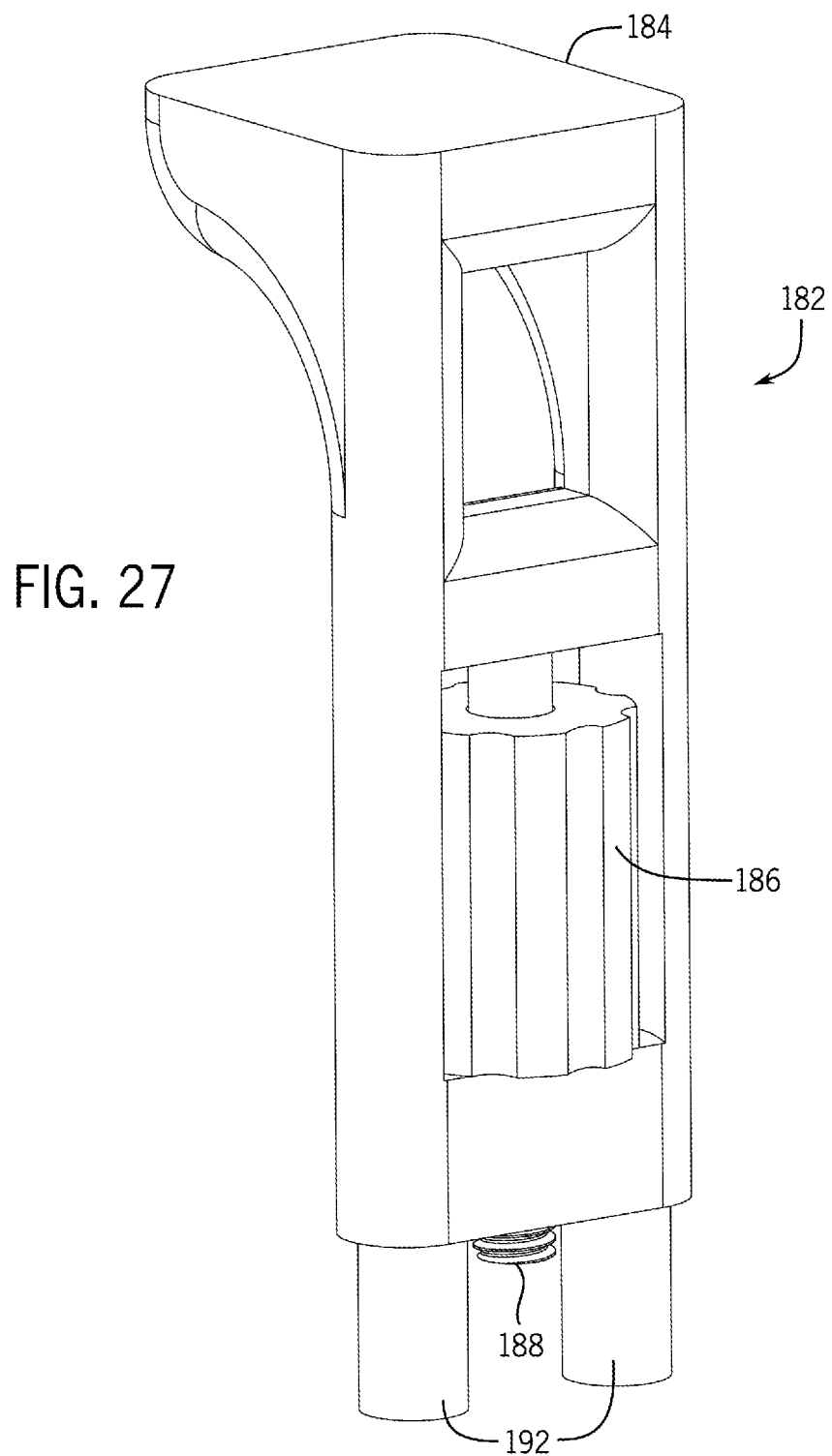
FIG. 27 illustrates a perspective view of an embodiment of a strike component.

Once prosthesis 10 and stem 12 are prepared for it implantation, stem insertion handle 166 can be lifted or otherwise removed from sizing block 158 and an insertion strike component 182 can be provided as shown in FIG. 27. At least one embodiment of strike component 182 includes a planar strike plate 184 and a screw mechanism 186 configured to twist screw 188 into a threaded aperture 190 extending through main body 168 of stem insertion handle 166, as shown in FIGS. 25A and 25B. At least one embodiment of strike component 182 can also include one or more fixation features 192 configured to be inserted into through-holes 180 of stem insertion handle 166. Fixation features 192 can serve to align strike component 182 with stem insertion handle 166 when coupling the two components together.

Figure 28:
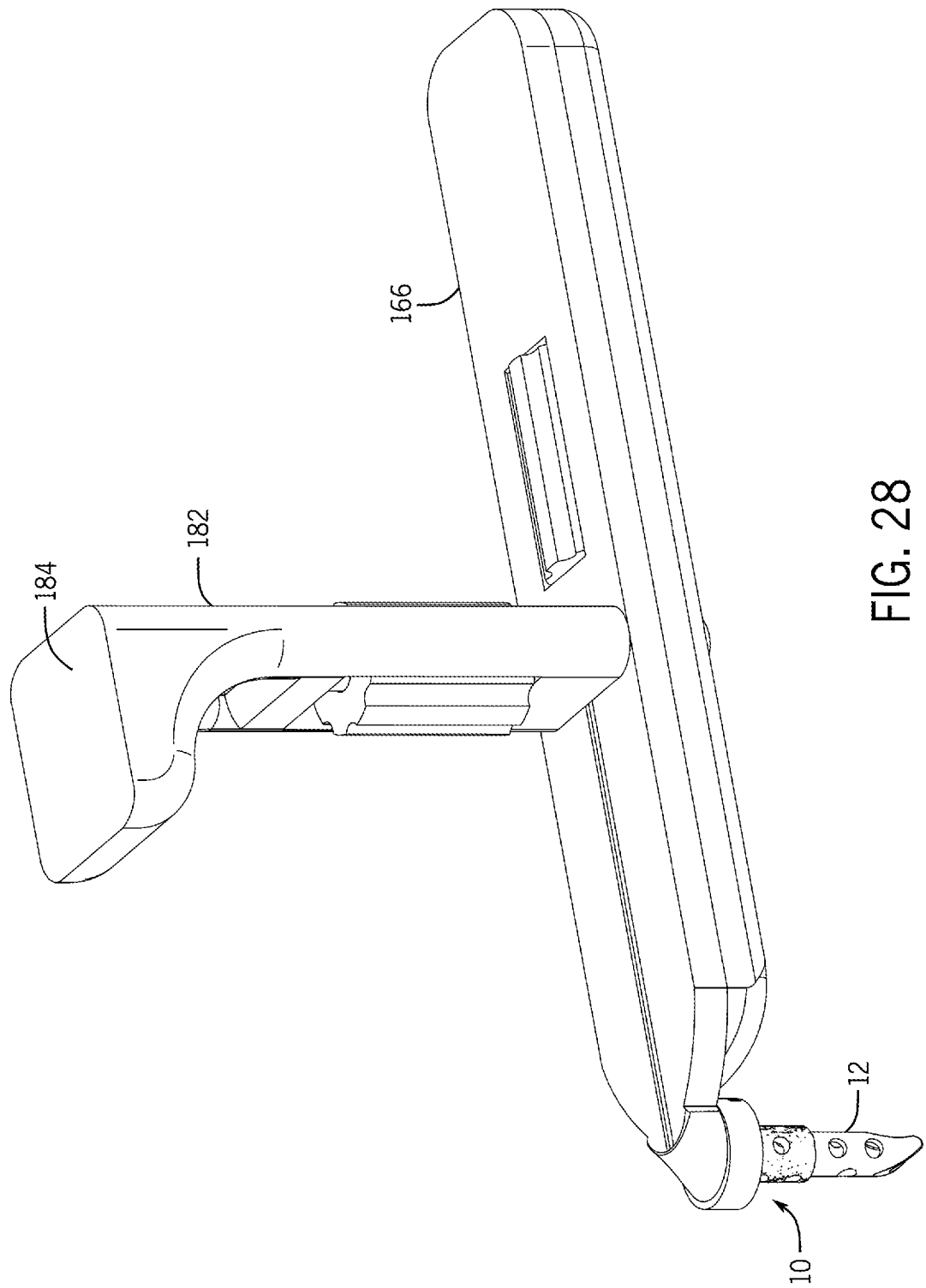
FIG. 28 illustrates a perspective view of an embodiment of a strike component coupled to an embodiment of a stem insertion handle.

FIG. 28 illustrates strike component 182 coupled to stem insertion handle 166, which is coupled to prosthesis 10. Thus coupled, the surgeon can strike against strike plate 184 or otherwise utilize the moment arms and mechanical advantages of strike component 182 and stem insertion handle 166 to push stem 12 of prosthesis 10 into the canal of the patient's radius during a radial head arthroplasty procedure.

Figure 29:
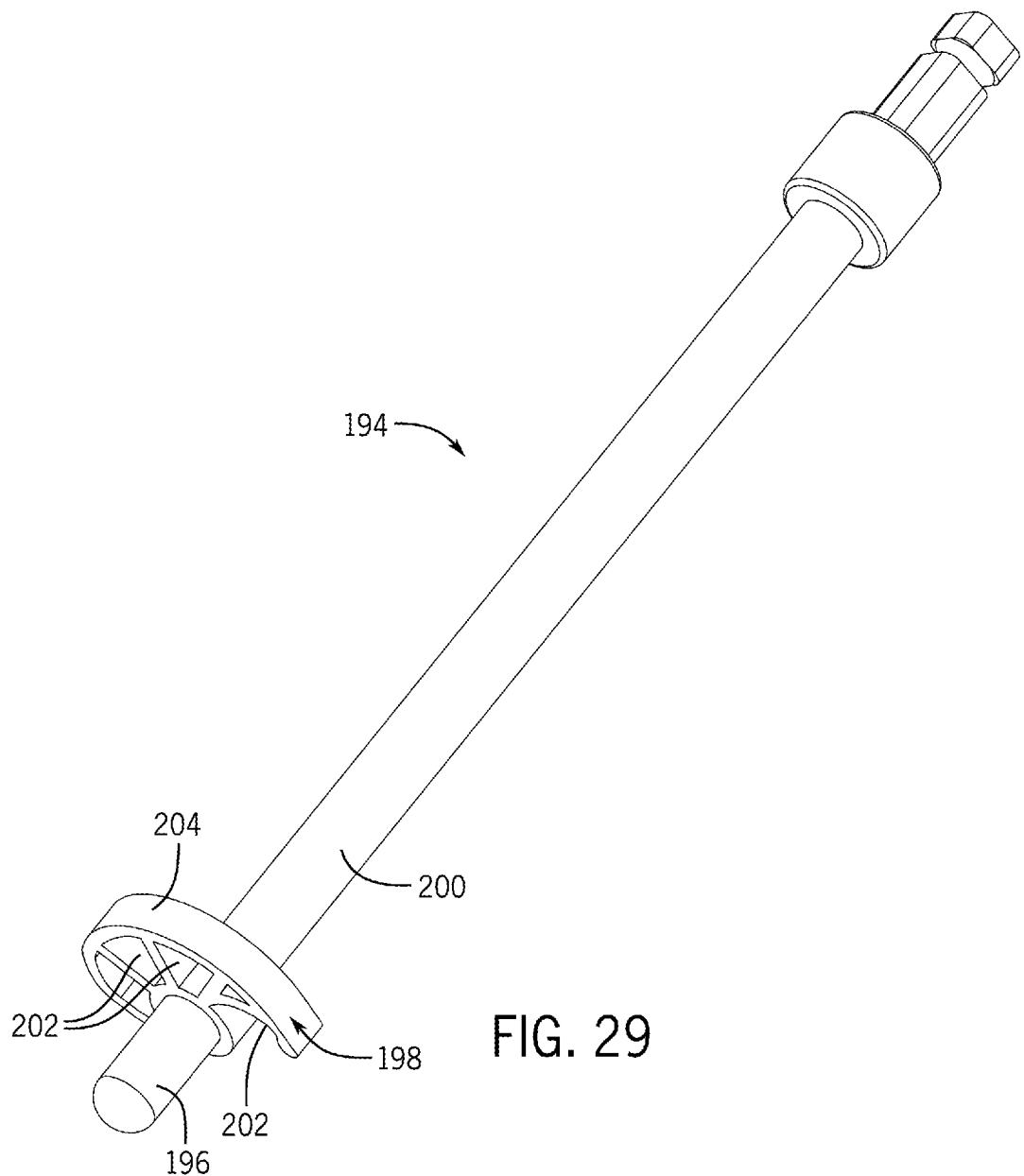
FIG. 29 illustrates a perspective view of an embodiment of a reamer.

In addition to other tools and devices described herein, an embodiment of a planer 194 is illustrated in FIG. 29. In at least one embodiment, planer 194 includes a planing assembly 198 extending radially outward from a main shaft 200. Planing assembly 198 can include a number of planing blades 202 extending outward from main shaft 200 to an outer wall 204 of planing assembly 198. In at least one embodiment, planing blades 202 can form a nautilus pattern.

Once a radial head of a patient's radius has been resected in the canal has been at least partially formed in the bone, a distal portion 196 of planer 194 can be inserted into the canal until planing blades 202 come into contact with the proximal resected surface of a radius bone. During use, the surgeon can press planing blades 202 against the top surface of a resected radius bone and rotate main shaft 200 to smooth or plain the top surface. Advantageously, planing assembly 198, including planing blades 202 and outer wall 204, form a compact mechanism that extends outward from main shaft 200 to generally match or only slightly exceed the surface area or outer circumference of a patient's radius. In this way, twisting shaft 200 to plain the proximal resected surface of the radius bone does not interfere with sensitive tissue such as nerves and other soft tissue surrounding the proximal end of the radius bone.

As noted above, each of the embodiments described in the detailed description above may include any of the features, options, and possibilities set out in the present disclosure, including those under the other independent embodiments, and may also include any combination of any of the features, options, and possibilities set out in the present disclosure and figures. Further examples consistent with the present teachings described herein are set out in the following numbered clauses:

Clause 1: A prosthesis comprising: a neck the neck comprising a sidewall extending circumferentially around the neck, an opening defined by the sidewall, and one or more interior surfaces defining a female receiving cavity; and a stem extending from the neck.

Clause 2: The prosthesis of clause 1, wherein a diameter of the neck is greater than a diameter of the stem.

Clause 3: The prosthesis of clauses 1 or 2, comprising: a radial head having a male protrusion extending from a lower surface of the radial head, and a screw coupling the radial head to the neck.

Clause 4: The prosthesis of clause 3, wherein the male protrusion is keyed to be received into the female receiving cavity.

Clause 5: The prosthesis of clauses 3 or 4, wherein the male protrusion is keyed to be received into the female receiving cavity through an opening defined by the sidewall of the neck.

Clause 6: The prosthesis of any of clauses 3 through 5, wherein: the screw includes a head and a shank; and the head includes first threads having a first thread pitch angle.

Clause 7: The prosthesis of clause 6, wherein: the shank includes second threads having a second thread pitch angle; and the first thread pitch angle is less than the second thread pitch angle.

Clause 8: The prosthesis of any of clauses 3 through 7, wherein the male protrusion includes an outwardly extending shelf portion.

Clause 9: The prosthesis of any of clauses 3 through 8, wherein the female receiving cavity includes a first portion and a second portion.

Clause 10: The prosthesis of clause 9, wherein at least one of the one or more interior surfaces of the neck includes an interior surface at least partially defining the second portion of the female receiving cavity.

Clause 11: The prosthesis of clause 10, wherein the male protrusion includes a shelf portion at least partially defined by an upper surface.

Clause 12: The prosthesis of clause 11, wherein the interior surface defining the second portion of the female receiving cavity is configured to press against the upper surface at least partially defining the shelf portion of the male protrusion to prevent the radial head from lifting away from the neck.

Clause 13: The prosthesis of any of clauses 1 through 12, further comprising a resection cap disposed in the female receiving cavity.

Clause 14: The prosthesis of clause 13, wherein the resection cap is keyed to be received through the opening defined by the sidewall of the neck.

Clause 15: The prosthesis of clause 13 or 14, wherein resection cap is keyed to be receiving into the female receiving cavity through the opening defined by the sidewall of the neck.

Clause 16: The prosthesis of any of clauses 13 through 15, wherein the resection cap includes an outwardly extending shelf portion.

Clause 17: The prosthesis of any of clauses 13 through 16, wherein the female receiving cavity includes a first portion and a second portion.

Clause 18: The prosthesis of clause 17, wherein at least one of the one or more interior surfaces of the neck includes an interior surface at least partially defining the second portion of the female receiving cavity.

Clause 19. The prosthesis of any of clauses 10 through 18, wherein the resection includes a shelf portion at least partially defined by an upper surface.

Clause 20: The prosthesis of clause 19, wherein the interior surface defining the second portion of the female receiving cavity is configured to press against the upper surface at least partially defining the shelf portion of the resection cap.

Clause 21: The prosthesis of clause 20, wherein the interior portion defining the second portion of the female receiving cavity is configured to prevent the radial head from lifting away from the neck.

Clause 22: The prosthesis of any of clauses 3 through 5 and 8 through 21, wherein: the screw includes a head and a shank; and the head includes first threads having a first thread pitch angle.

Clause 23: The prosthesis of clause 22, wherein: the shank includes second threads having a second thread pitch angle; and the first thread pitch angle is less than the second thread pitch angle.

Clause 24: The prosthesis of clause 23, wherein: the male protrusion defines a through-hole having an internal thread complimentary to the first threads of the head of the screw; the neck defines a hole having an internal thread complimentary to the second threads of the shank of the screw.

Clause 25: The prosthesis of clause 24, wherein the screw couples the radial head to the neck with the head of the screw engaging the through-hole defined by the male protrusion and the shank of the screw engaging the hole defined by the neck.

Clause 26: The prosthesis of any of clauses 1 through 25, further comprising a resection cap disposed in the female receiving cavity, an upper surface of the cap being generally co-planar with an upper surface of the neck.

Clause 27: The prosthesis of clause 26, wherein the resection cap includes an outer side surface that is flush with the sidewall of the neck.

Clause 28: The prosthesis of any of clauses 1 through 25 and 27, the neck comprising an upper surface that defines an upper opening to the female receiving cavity.

Clause 29: The prosthesis of clause 28, wherein the upper opening defines a tapered channel.

Clause 30: The prosthesis of clause 29, further comprising a radial head having a male protrusion extending from a lower surface of the radial head, the male protrusion at least partially defined by a first exterior surface, wherein the first exterior surface forms a tapered geometry complimentary to the tapered channel of the upper opening.

Clause 31: A method of implanting a prosthesis, comprising: inserting a male protrusion of a radial head component into a female receiving cavity of a prosthesis through an opening in a sidewall of the prosthesis, wherein the prosthesis comprises a prosthesis of any of clauses 1 through 31.

Clause 32: A radial head prosthetic device, comprising: a stem extending from a neck, the neck having a sidewall defining an opening configured to receive a male protrusion of a second component.

Clause 33: The radial head prosthetic device of clause 32, wherein the second component comprises a radial head.

Clause 34: The radial head prosthetic device of clause 32, wherein the second component comprises a resection cap.

Clause 35: The radial head prosthetic device of clause 34, wherein the resection cap comprises an upper surface that is generally flush with an upper surface of the neck.

Clause 36: A method of resecting a radial head prosthetic, the method comprising: removing a prosthetic radial head from a stem by pulling the radial head laterally outward from the stem, the stem having a neck with a sidewall defining an opening; and inserting a resection cap into the neck through the opening in the sidewall of the neck.

Clause 37: The method of clause 36, further comprising coupling the resection cap to the neck of the stem with a screw.

Clause 38: The method of clause 36 or 37, wherein the stem is not removed from a patient's bone.

Clause 39: A radial head prosthesis, comprising: a neck comprising: a sidewall extending circumferentially around the neck; an opening defined by the sidewall; and one or more interior surfaces defining a female receiving cavity; and a hollow stem extending from the neck, the hollow stem defining an inner volume.

Clause 40: The radial head prosthesis of clause 39, further comprising one or more apertures extending through a perimeter wall of the hollow stem, the perimeter wall having an interior surface at least partially defining the inner volume.

Clause 41: The radial head prosthesis of clauses 39 or 40, the hollow stem having a textured proximal portion.

Clause 42: The radial head prosthesis of any of clauses 39 through 41, the stem comprising a distal portion having a hooked geometry.

Clause 43: The radial head prosthesis of any of clauses 39, wherein a distal end of the stem is open.

Clause 44: A radial head sizing tool, comprising a first stop surface having a male protrusion extending from the first stop surface, the first stop surface being distally located on the radial head sizing tool.

Clause 45: The radial head sizing tool of clause 44, further comprising a second stop surface movable relative to the first stop surface, the second stop surface being distally located on the radial head sizing tool.

Clause 46: The radial head sizing tool of clause 45, further comprising: proximally located finger grips; overlapping portions extending from the finger grips, the overlapping portions including calibrated measurement indicia indicating a distance between the first stop surface and the second stop surface.

Clause 47: A method of measuring a distance between a proximal end of a radius and a distal end of a humerus, the method comprising: inserting the male protrusion of the radial sizing head of clause 45 into a female receiving cavity of a temporary sizing neck, the temporary sizing neck having a lower protrusion; placing a lower surface of the temporary sizing neck against a proximal surface of the radius so that the lower protrusion of the temporary sizing neck extends into a canal of the radius; moving the second stop surface away from the first stop surface until the second stop surface contacts the distal end of the humerus.

Clause 48: A reamer, comprising a distal portion extending from a shaft, the distal portion including a proximal section and a distal section, wherein: the proximal section is ribbed and has a diameter of 7 mm; the distal section is threaded and has a diameter of 6 mm.

Clause 49: The reamer of clause 48, wherein the proximal section has a length of 10 mm and the distal section has a length of 17 mm.

Clause 50: A reamer system, comprising: a first reamer having a first distal portion extending from a first shaft, the first distal portion including a first proximal section having a first diameter and a first distal section having a second diameter; and a second reamer having a second distal portion extending from a second shaft, the second distal portion including a second proximal section having a third diameter and a second distal section having a fourth diameter, wherein: the first diameter is less than the third diameter; the second diameter is less than the fourth diameter; and a first ratio including the first diameter over the second diameter is less than a second ratio including the third diameter over the fourth diameter.

Clause 51: A graft packer, comprising a cavity configured to receive a stem of a prosthetic, the cavity including rifled features.

Clause 52: A prosthetic preparation system, comprising: a sizing block comprising: one or more sizing recesses; one or more fixation features; and a recessed portion; a stem insertion handle comprising: a male protrusion configured to be received by a female receiving cavity of a prosthetic stem; a screw mechanism configured to couple the male protrusion to the prosthetic stem, wherein the recessed portion of the sizing block receives a portion of the screw mechanism when the stem insertion handle is coupled to the sizing block; one or more through-holes extending through a main body of the stem insertion handle, wherein at least one of the one or more fixation features of the sizing block extends at least partially into at least one of the one or more through-holes when the stem insertion handle is coupled to the sizing block.

Clause 53: The prosthetic preparation system of clause 52, the stem insertion handle further comprising a threaded aperture.

Clause 54: The prosthetic preparation system of clause 53, further comprising a strike component including fixation feature and a screw mechanism including a screw, wherein the screw is configured to be threaded into the threaded aperture of the stem insertion handle to couple the strike component to the stem insertion handle.

Clause 55: The prosthetic preparation system of clause 54, wherein the fixation feature is configured to be at least partially inserted into at least one of the one or more through-holes of the stem insertion handle when the strike component is coupled to the stem insertion handle.

Clause 56: The prosthetic preparation system of clause 54 or 55, the strike component further comprising a strike plate.

Clause 57: A bone planer, comprising: an elongate shaft; a distal portion extending from the elongate shaft; and a planing assembly disposed distally on the elongate shaft and proximal to the distal portion.

Clause 58: The bone planer of clause 57, the planing assembly comprising planing blades and an outer wall, the planing blades extending outward from the shaft to the outer wall.

Clause 59: The bone planer clause 58, wherein the planing blades form a nautilus pattern.

Clause 60: A prosthesis, comprising: a neck defining a sidewall extending circumferentially around the neck, the sidewall defining a sidewall opening; a female receiving cavity defined by one or more interior surfaces extending into the neck from the sidewall opening; and a stem extending from the neck.

Clause 61: The prosthesis of clause 60, wherein a diameter of the neck is greater than a diameter of the stem.

Clause 62: The prosthesis of clause 60 or 61, wherein the neck defines an upper surface disposed perpendicular to the sidewall, the upper surface defining an upper opening.

Clause 63: The prosthesis of clause 62, wherein a first surface of the one or more interior surfaces extends downward into the neck from the upper opening to form a first portion of the female cavity.

Clause 64: the prosthesis of clause 63, wherein a second portion of the female receiving cavity is at least partially defined by a second surface of the one or more interior surfaces, the second surface extending laterally outward from the first surface.

Clause 65: The prosthesis of clause 63 or 64, further comprising a hole defined by the first surface and extending into the neck from the first surface.

Clause 66: The prosthesis of any of clauses 60 through 65, wherein the sidewall opening forms a keyed geometry configured to receive a male protrusion of a radial head having a complimentary keyed geometry.

Clause 67: A prosthesis, comprising: a neck defining an upper surface and a sidewall extending downward from the upper surface; an opening defined by the sidewall and extending into the neck, the opening having an upper portion and a lower portion, wherein the lower portion extends laterally beyond a width of the upper portion.

Clause 68: The prosthesis of clause 67, further comprising at least one interior surface extending into the neck from the opening to define a female receiving cavity.

Clause 69: The prosthesis of clause 68, further comprising a radial head defining a lower surface and a male protrusion extending from the lower surface.

Clause 70: The prosthesis of clause 69, wherein the male protrusion is configured to be received into the female receiving cavity.

Clause 71: The prosthesis of clause 69 or 70, wherein the male protrusion forms a keyed geometry to be received into the female receiving cavity through the opening.

Clause 72: The prosthesis of clauses 69 through 71, wherein: a first surface of the at least one interior surface defines a first threaded hole extending into the neck; the male protrusion defines a second threaded hole extending into the male protrusion, the second threaded hole aligning with the first threaded hole when the male protrusion is received into the female receiving cavity.

Clause 73: The prosthesis of clause 72, further comprising a screws extending through the first and second threaded holes, the screw including a head and a shank, wherein: the head includes first threads having a first thread pitch angle; the shank includes second threads having a second thread pitch angle; and the first thread pitch angle is less than the second thread pitch angle.

Clause 74: The prosthesis of any of clauses 68 through 73, further comprising a resection cap disposed in the female receiving cavity, the resection cap defining an upper surface that is flush with the upper surface defined by the neck.

Clause 75: A prosthetic device, comprising: a neck defining an upper surface and a sidewall extending from the upper surface; an opening defined by the sidewall and extending into the neck; one or more interior surfaces extending into the neck from the opening to define a female receiving cavity; and a radial head including a male protrusion received within the female receiving cavity through the opening.

Clause 76: The prosthetic device of clause 75, further comprising a hollow stem extending from the neck, the hollow stem defining an inner volume.

Clause 77: The prosthetic device of clause 76, further comprising one or more apertures extending through a perimeter wall of the hollow stem, the perimeter wall having an interior surface at least partially defining the inner volume.

Clause 78: The prosthetic device of clauses 76 or 77, the stem comprising a distal portion having a hooked geometry.

Clause 79: The prosthetic device of any of clauses 76 through 78, wherein a distal end of the stem is open.

The articles "a," "an," and "the" are intended to mean that there are one or more of the elements in the preceding descriptions. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features. Numbers, percentages, ratios, or other values stated herein are intended to include that value, and also other values that are "about" or "approximately" the stated value, as would be appreciated by one of ordinary skill in the art encompassed by embodiments of the present disclosure. A stated value should therefore be interpreted broadly enough to encompass values that are at least close enough to the stated value to perform a desired function or achieve a desired result. The stated values include at least the variation to be expected in a suitable manufacturing or production process, and may include values that are within 5%, within 1%, within 0.1%, or within 0.01% of a stated value.

A person having ordinary skill in the art should realize in view of the present disclosure that equivalent constructions do not depart from the spirit and scope of the present disclosure, and that various changes, substitutions, and alterations may be made to embodiments disclosed herein without departing from the spirit and scope of the present disclosure. Equivalent constructions, including functional "means-plus-function" clauses are intended to cover the structures described herein as performing the recited function, including both structural equivalents that operate in the same manner, and equivalent structures that provide the same function. It is the express intention of the applicant not to invoke means-plus-function or other functional claiming for any claim except for those in which the words 'means for' appear together with an associated function. Each addition, deletion, and modification to the embodiments that falls within the meaning and scope of the claims is to be embraced by the claims.

The terms "approximately," "about," and "substantially" as used herein represent an amount close to the stated amount that still performs a desired function or achieves a desired result. For example, the terms "approximately," "about," and "substantially" may refer to an amount that is within less than 5% of, within less than 1% of, within less than 0.1% of, and within less than 0.01% of a stated amount. Further, it should be understood that any directions or reference frames in the preceding description are merely relative directions or movements. For example, any references to "up" and "down" or "above" or "below" are merely descriptive of the relative position or movement of the related elements.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed is:

1. A prosthesis, comprising:
   a neck defining a sidewall extending circumferentially around the neck, the sidewall defining a sidewall opening;
   a female receiving cavity defined by one or more interior surfaces extending into the neck from the sidewall opening, a first surface of the one or more interior surfaces defining a first threaded hole extending into the neck;
   a stem extending from the neck; and
   a radial head defining a lower surface and a male protrusion extending from the lower surface, the male protrusion defining a second threaded hole extending into the male protrusion, the second threaded hole configured to align with the first threaded hole when the male protrusion is received into the female receiving cavity; and
   a screw configured to extend through the first and second threaded holes, the screw including a head and a shank, wherein:
     the head includes first threads having a first thread pitch angle;
     the shank includes second threads having a second thread pitch angle; and
     the first thread pitch angle is less than the second thread pitch angle.

2. The prosthesis of claim 1, wherein a diameter of the neck is greater than a diameter of the stem.

3. The prosthesis of claim 1, wherein the neck defines an upper surface disposed perpendicular to the sidewall, the upper surface defining an upper opening.

4. The prosthesis of claim 3, wherein the first surface of the one or more interior surfaces extends downward into the neck from the upper opening to form a first portion of the female cavity.

5. The prosthesis of claim 4, wherein a second portion of the female receiving cavity is at least partially defined by a second surface of the one or more interior surfaces, the second surface extending laterally outward from the first surface.

6. The prosthesis of claim 1, wherein the sidewall opening forms a keyed geometry configured to receive a male protrusion of a radial head having a complimentary keyed geometry.

7. A prosthesis comprising:
   a neck defining an upper surface and a sidewall extending downward from the upper surface;
   an opening defined by the sidewall and extending into the neck, the opening having an upper portion and a lower portion, wherein the lower portion extends laterally beyond a width of the upper portion;
   further comprising at least one interior surface extending into the neck from the opening to define a female receiving cavity; and
   a resection cap configured to be disposed in the female receiving cavity such that the resection cap defines an upper surface that is flush with the upper surface defined by the neck when the resection cap is disposed in the female receiving cavity.

8. The prosthesis of claim 7, further comprising a radial head defining a lower surface and a male protrusion extending from the lower surface.

9. The prosthesis of claim 8, wherein the male protrusion is configured to be received into the female receiving cavity.

10. The prosthesis of claim 8, wherein the male protrusion forms a keyed geometry to be received into the female receiving cavity through the opening.

11. The prosthesis of claim 8, wherein:
a first surface of the at least one interior surface defines a first threaded hole extending into the neck;
the male protrusion defines a second threaded hole extending into the male protrusion, the second threaded hole aligning with the first threaded hole when the male protrusion is received into the female receiving cavity.

12. The prosthesis of claim 11, further comprising a screw extending through the first and second threaded holes, the screw including a head and a shank, wherein:
the head includes first threads having a first thread pitch angle;
the shank includes second threads having a second thread pitch angle; and
the first thread pitch angle is less than the second thread pitch angle.

13. A prosthetic device, comprising:
a neck defining an upper surface and a sidewall extending from the upper surface;
an opening defined by the sidewall and extending into the neck;
one or more interior surfaces extending into the neck from the opening to define a female receiving cavity;
a radial head including a male protrusion received within the female receiving cavity through the opening;
a threaded through hole defined by and extending through the male protrusion and having a first thread pitch angle; and
a threaded hole defined by and extending into the neck from the one or more interior surfaces, the threaded hole having a second thread pitch angle different than the first thread pitch angle.

14. The prosthetic device of claim 13, further comprising a hollow stem extending from the neck, the hollow stem defining an inner volume.

15. The prosthetic device of claim 14, further comprising one or more apertures extending through a perimeter wall of the hollow stem, the perimeter wall having an interior surface at least partially defining the inner volume.

16. The prosthetic device of claim 14, the stem comprising a distal portion having a hooked geometry.

17. The prosthetic device of claim 14, wherein a distal end of the stem is open.

* * * * *